(12) United States Patent
Al-Ali et al.

(10) Patent No.: US 8,560,032 B2
(45) Date of Patent: Oct. 15, 2013

(54) NONINVASIVE MULTI-PARAMETER PATIENT MONITOR

(75) Inventors: Ammar Al-Ali, Tustin, CA (US); Joe E. Kiani, Laguna Niguel, CA (US); Mohamed Diab, Mission Viejo, CA (US); Roger Wu, Irvine, CA (US); Rick Fishel, Orange, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

(21) Appl. No.: 13/477,975

(22) Filed: May 22, 2012

(65) Prior Publication Data

US 2012/0232363 A1     Sep. 13, 2012

Related U.S. Application Data

(63) Continuation-in-part of application No. 11/367,014, filed on Mar. 1, 2006, now Pat. No. 8,224,411.

(60) Provisional application No. 60/657,596, filed on Mar. 1, 2005, provisional application No. 60/657,281, filed on Mar. 1, 2005, provisional application No. 60/657,268, filed on Mar. 1, 2005, provisional application No. 60/657,759, filed on Mar. 1, 2005.

(51) Int. Cl.
  *A61B 5/1455*     (2006.01)
(52) U.S. Cl.
  USPC .......................................... 600/310; 600/322
(58) Field of Classification Search
  USPC ................................................ 600/310–344
  See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,188,108 A * | 2/1993 | Secker ..................... | 600/310 |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |

(Continued)

FOREIGN PATENT DOCUMENTS

| | | |
|---|---|---|
| JP | 10-500026 | 6/1998 |
| JP | 2004-510467 | 8/2004 |
| WO | WO 9516387 | 6/1995 |
| WO | WO 0217780 | 3/2002 |

*Primary Examiner* — Eric Winakur
*Assistant Examiner* — Marjan Fardanesh
(74) *Attorney, Agent, or Firm* — Knobbe Martens Olson & Bear LLP

(57) ABSTRACT

Embodiments of the present disclosure include a handheld multi-parameter patient monitor capable of determining multiple physiological parameters from the output of a light sensitive detector capable of detecting light attenuated by body tissue. For example, in an embodiment, the monitor is capable of advantageously and accurately displaying one or more of pulse rate, plethysmograph data, perfusion quality, signal confidence, and values of blood constituents in body tissue, including for example, arterial carbon monoxide saturation ("HbCO"), methemoglobin saturation ("HbMet"), total hemoglobin ("Hbt"), arterial oxygen saturation ("SpO$_2$"), fractional arterial oxygen saturation ("SpaO$_2$"), or the like. The monitor can determine which a plurality of light emitting sources and which of a plurality of parameters to measure based on the signal quality and resources available.

19 Claims, 18 Drawing Sheets

(56) References Cited

U.S. PATENT DOCUMENTS

| | | |
|---|---|---|
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |

(56) References Cited

U.S. PATENT DOCUMENTS

| | | |
|---|---|---|
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 2002/0035315 A1* | 3/2002 | Ali et al. ............. 600/300 |

\* cited by examiner

NONINVASIVE MULTI-PARAMETER PATIENT MONITOR

PRIORITY CLAIM TO RELATED PROVISIONAL APPLICATIONS

The present application is a continuation-in-part of U.S. patent application Ser. No. 11/367,014, filed on Mar. 1, 2006, now U.S. Pat. No. 8,224,411 which claims priority benefit under 35 U.S.C. §119(e) to U.S. Provisional Patent Application Ser. No. 60/657,596, filed Mar. 1, 2005, entitled "Multiple Wavelength Sensor," No. 60/657,281, filed Mar. 1, 2005, entitled "Physiological Parameter Confidence Measure," No. 60/657,268, filed Mar. 1, 2005, entitled "Configurable Physiological Measurement System," and No. 60/657,759, filed Mar. 1, 2005, entitled "Noninvasive Multi-Parameter Patient Monitor." The present application incorporates the foregoing disclosures herein by reference.

INCORPORATION BY REFERENCE OF RELATED UTILITY APPLICATIONS

The present application is related to the following copending U.S. utility applications:

|    | App. Sr. No. | Filing Date   | Title                                                          |
|----|--------------|---------------|----------------------------------------------------------------|
| 1  | 11/367,013   | Mar. 1, 2006  | Multiple Wavelength Sensor Emitters                            |
| 2  | 11/366,995   | Mar. 1, 2006  | Multiple Wavelength Sensor Equalization                        |
| 3  | 11/366,209   | Mar. 1, 2006  | Multiple Wavelength Sensor Substrate                           |
| 4  | 11/366,210   | Mar. 1, 2006  | Multiple Wavelength Sensor Interconnect                        |
| 5  | 11/366,833   | Mar. 1, 2006  | Multiple Wavelength Sensor Attachment                          |
| 6  | 11/366,997   | Mar. 1, 2006  | Multiple Wavelength Sensor Drivers                             |
| 7  | 11/367,034   | Mar. 1, 2006  | Physiological Parameter Confidence Measure                     |
| 8  | 11/367,036   | Mar. 1, 2006  | Configurable Physiological Measurement System                  |
| 9  | 11/367,033   | Mar. 1, 2006  | Noninvasive Multi-Parameter Patient Monitor                    |
| 10 | 11/367,014   | Mar. 1, 2006  | Noninvasive Multi-Parameter Patient Monitor                    |
| 11 | 11/366,208   | Mar. 1, 2006  | Noninvasive Multi-Parameter Patient Monitor                    |
| 12 | 13/412,428   | Mar. 5, 2012  | Noninvasive Multi-Parameter Patient Monitor                    |
| 13 | 12/949,271   | Nov. 18, 2010 | Physiological Measurement System with Automatic Wavelength Adjustment |

The present application incorporates the foregoing disclosures herein by reference.

FIELD OF THE DISCLOSURE

The present disclosure relates to the field of noninvasive patient monitors. More specifically, the disclosure relates to monitors displaying measurements derived using signals from optical sensors.

BACKGROUND

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{0,\lambda}} \tag{1}$$

$$\mu_{0,\lambda} = \sum_{i=1}^{n} \epsilon_{i,\lambda} \cdot c_i \tag{2}$$

where $\mu_{0,\lambda}$ is the bulk absorption coefficient and represents the probability of absorption per unit length. The minimum number of discrete wavelengths that are required to solve Equations 1-2 are the number of significant absorbers that are present in the solution.

A practical application of this technique is pulse oximetry, which utilizes a noninvasive sensor to measure oxygen saturation ($SpO_2$) and pulse rate. In general, the sensor has light emitting diodes (LEDs) that transmit optical radiation of red and infrared wavelengths into a tissue site and a detector that responds to the intensity of the optical radiation after absorption (e.g., by transmission or transreflectance) by pulsatile arterial blood flowing within the tissue site. Based on this response, a processor determines measurements for $SpO_2$, pulse rate, and can output representative plethysmographic waveforms. Thus, "pulse oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood.

Pulse oximeters capable of reading through motion induced noise are available from Masimo Corporation ("Masimo") of Irvine, Calif. Moreover, portable and other oximeters capable of reading through motion induced noise are disclosed in at least U.S. Pat. Nos. 6,770,028, 6,658,276, 6,157,850, 6,002,952, and 5,769,785. Read which are owned by Masimo, and are incorporated by reference herein. Such reading through motion oximeters have gained rapid acceptance in a wide variety of medical applications, including surgical wards, intensive care and neonatal units, general wards, home care, physical training, and virtually all types of monitoring scenarios.

SUMMARY OF THE DISCLOSURE

Despite the success of read through motion oximeter systems, there is a need to provide patient monitors capable of displaying multiple physiological parameters, other than or in addition to $SpO_2$, plethysmograph waveforms, or pulse rates. For example, in accessing a patient's condition, caregivers often desire knowledge of other blood constituents, including for example, a percent value for arterial carbon monoxide saturation ("HbCO") or a percent value for methemogobin saturation ("HbMet") or the like. For example, in an embodiment, the display advantageously displays one or more of the following: pulse rate, plethysmograph waveform data, perfusion index, values of blood constituents in body tissue, including for example, HbCO, HbMet, total hemoglobin ("Hbt"), arterial oxygen saturation ("SpO$_2$"), fractional arterial oxygen saturation ("SpaO$_2$"), or the like. In other embodiments, the monitor may advantageously and accurately determine values for one or more of HbO$_2$, Hb, blood glucose, water, the presence or absence of therapeutic drugs (aspirin, Dapson, nitrates, or the like) or abusive/recreational drugs (methamphetamine, alcohol, steroids, or the like), concentrations of carbon dioxide ("CO$_2$") or oxygen ("O"), ph levels, bilirubin, perfusion quality, signal quality or the like. Accordingly, the present disclosure includes a multi-parameter patient monitor capable of determining one or more of the foregoing parameters, other than or in addition to, SpO$_2$, plethysmograph waveforms, or perfusion quality index.

In an embodiment, the display of a noninvasive multi-parameter patient monitor advantageously includes a plurality of display modes enabling more parameter data to be displayed than the available physical display area or real estate. In an embodiment, a user may cycle different parameter values through an area of the display common to both parameters even when one parameter is shifted, through, for example, actuation of a user input key. The patient monitor may also display different parameters as color-coded. For example, when the following measured parameters are within "normal" ranges, SpO$_2$ may be displayed red, pulse rate (BPM) may be displayed green, HbCO may be displayed orange, HbMet may be displayed blue, or the like. In an embodiment, measured values of SpO$_2$ may be displayed in white, BPM may be displayed in yellow green or aquamarine, PI™ may be displayed in violet, Hbt may be displayed in grass green, HbMet may be displayed in blue or light blue, HbCO may be displayed in orange, and SpaO$_2$ may be displayed in electric blue.

Moreover, parameter trend data may also be displayed using the same or similar color coding, especially when multiple trends are displayed on one or more display graphs. In addition, more coarse or gross parameter indications may be displayed for quick reference to indicate to a caregiver whether any of a variety of monitored parameters, such as, for example, SpO$_2$, HbCO or HbMet is within acceptable ranges. The monitor may advantageously include additional display information, such as, for example, parametric displays where one parameter is displayed as a function of another, three dimensional displays (for example, extending a parametric display along time or an additional parameter), directional indicators predicting where a parameter is likely heading or reporting a general direction a parameters has been trending, or the like.

In addition to the foregoing, caregivers often desire to more closely monitor parameters that are close to, approaching, or beyond normal safe thresholds. In an embodiment, the patient monitor provides an indication that the caregiver should change display modes to view more critical monitored parameters. In alternative embodiments, the patient monitor automatically changes display modes to show parameters moving closer to or beyond normal thresholds.

In an embodiment, the patient monitor includes an audible or visual indication of a type of sensor communicating with the monitor. For example, the monitor may determine how many wavelengths a particular attached sensor will emit through communication with memory devices associated with the attached sensor or cable.

Additional embodiments include audio or visual alarms for each of multiple monitored parameters, combinations of parameters, an indication of perfusion in the tissue of the measurement site, an indication of the confidence the signal processing has in its output measurements, or the like.

For purposes of summarization, certain aspects, advantages and novel features are described herein. Of course, it is to be understood that not necessarily all such aspects, advantages or features need to be present in any particular embodiment.

In an embodiment, a method of determining which of a plurality of physiological measurements to measure based on the signal quality of the signal is disclosed. The method includes using a sensor configured to measure at least two different physiological measurements to obtain a signal from a light sensitive detector, the sensor including at least three different light emitters emitting at least three different wavelengths of light through tissue of a living patient and detecting the light after attenuation of the tissue, determining a signal quality of the signal, determining which of the at least two different physiological measurements are capable of being measured based on the signal quality determination, and activating only enough of the at least three different light emitters necessary to obtain the measurements capable of being measured. In an embodiment, if the signal quality is high, all of the at least three different emitters are activated. In an embodiment, if the signal quality is low, only two of the at least three different emitters are activated. In an embodiment, if the signal quality is low, fewer different physiological measurements are measured.

In an embodiment, a method of informing a user of a patient monitor about one of a type of sensor communicating with the patient monitor and a type of physiological parameter determinable using the sensor communicating with the patient monitor is disclosed. The method includes receiving information from an information element associated with one of an optical sensor and a communication cable between a patient monitor and an optical sensor, determining a number of wavelengths emitted by the optical sensor from the information, determining a signal quality of a signal received by the optical sensor, and activating an indicator of the type of physiological parameters determinable based on the number wavelengths emitted by the optical sensor and the signal quality of the signal. In an embodiment, the indicator comprises a display of data determined using signals from the optical sensor. In an embodiment, the indicator comprises a visual indicator. In an embodiment, the visual indicator comprises a color. In an embodiment, the visual indicator comprises an LED. In an embodiment, the LED changes color based on which of the first and second sensors is attached. In an embodiment, the LED color comprises red when the first sensor is attached and another color when another sensor is attached. In an embodiment, the indicator comprises an audible indicator. In an embodiment, the audible indictor comprises one or more tones.

In an embodiment, the audible indictor emits a first tone when the first sensor is attached and a different second tone when the second sensor is attached.

BRIEF DESCRIPTION OF THE DRAWINGS

The drawings and the associated descriptions are provided to illustrate embodiments of the disclosure and not to limit the scope of the claims.

DETAILED DESCRIPTION OF PREFERRED AND ALTERNATIVE EMBODIMENTS

Figure 1:
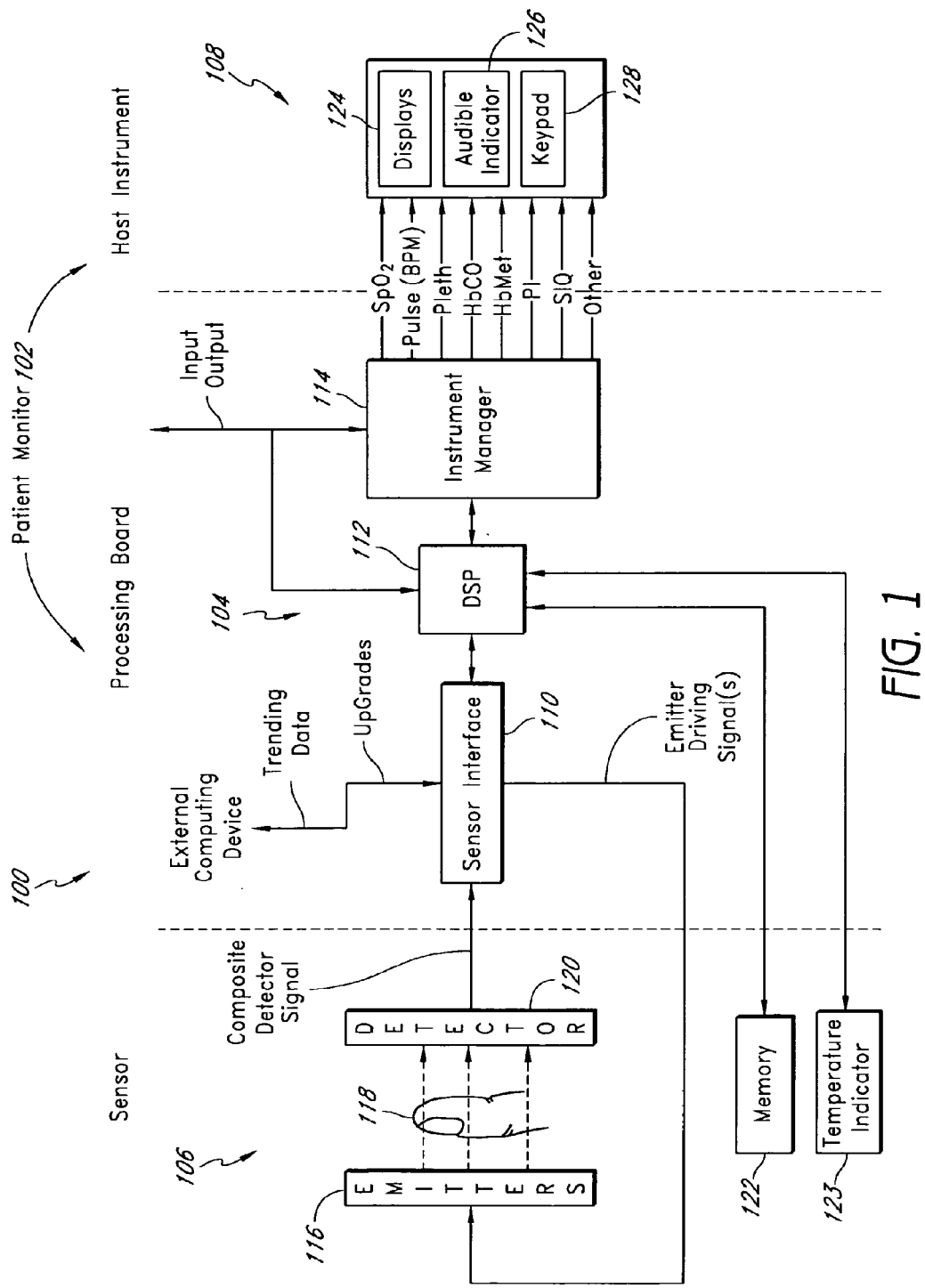
FIG. 1 illustrates a block diagram of an exemplary embodiment of a patient monitoring system including a sensor and a multi-parameter patient monitor.

Embodiments of the present disclosure include a portable or other multi-parameter patient monitor capable of determining multiple physiological parameters from one or more signals output from one or more light sensitive detectors capable of detecting light attenuated by body tissue carrying pulsing blood. For example, in an embodiment, the monitor advantageously and accurately determines a wide variety of physiological parameters or other calculations as discussed above.

In an embodiment, the display of patient monitor advantageously includes a plurality of display modes enabling more parameter data to be displayed than the available physical display real estate. For example, the patient monitor may include one or more user input keys capable of toggling through measurement data. In an embodiment, the displays include mode indicators providing caregivers easily identifiable visual queues, such as LED's, text, icons, or other indicia providing readily identifiable queues as to which parameter is being displayed. In an embodiment, the display may shift, may be parameter color-coded, or the like to further ensure quick comprehension of which measured parameter is the displayed parameter. For example, in an embodiment, the monitor displays $SpO_2$ in white, pulse rate (BPM) in green, HbCO in orange, and HbMet in blue when the respective measured parameter is within a "normal" range.

In an embodiment, the patient monitor provides an indication that the caregiver should change display modes to view more critical or time sensitive measured parameters, specific caregiver selected parameters, or the like. For example, the patient monitor may advantageously sound audio or visual alarms that alert the caregiver to particular one or more of worsening parameters, parameters changing in a predetermined pattern or rate, parameters stabilizing below user defined or safe thresholds, caregiver selected parameters, or the like. The monitor may also use alerts that provide audio or visual indications of the severity of the condition, severity of the change, or the like. In alternative embodiments, the patient monitor may automatically change display modes when a particular parameter crosses one or more thresholds. For example, a patient monitor may be displaying a first parameter, such as a plethysmograph, and upon determining measurements indicating that HBMet is trending toward an alarm condition, the monitor may automatically switch from displaying the first parameter to the alarming parameter, or in this case, a trend of the alarming parameter.

In an embodiment, a switch is provided to allow a user to switch displays to view an alarming measurement. In an embodiment, during an alarm condition, a parameter display may switch to a trend graph in the same or different color, line weight, flash, flash rate, intensity, size, or the like.

The patient monitor may also include one or more displays capable of displaying trend data for any one or more of the monitored or derived patient parameters. For example, the trend data may be displayed in graph form, may include multiple trend lines, each representing a different monitored or derived patient parameter. Moreover, each trend line may be color-coded to facilitate quick comprehension of which trend line represents which measured parameter. However, an artisan will recognize from the disclosure herein a large number of identification techniques including color-coding, identifying text, or the like. Additionally, user input may toggle displayed trend data, may select which parameters to display simultaneously, or the like.

In an embodiment, the patient monitor includes an audible or visual indication of a type of sensor communicating with the monitor. For example, the patient monitor may provide a particular audio or visual indication, such as a beep, LED activation, graphic activation, text messages, voice messages, or the like, to indicate communication with or connection to an approved sensor, patient cable, combination, or the like. In an embodiment, the indication may change based on the manufacturer, type of sensor recognized or not recognized, type of patient, type of physiological parameters measurable with the attached sensor, or the like. Additional embodiments include an indication of perfusion in the tissue of the measurement site and an indication of the confidence the signal processing has in its output measurements or input signal quality.

To facilitate an understanding of the disclosure, the remainder of the description references exemplary embodiments illustrated in the drawings. Moreover, in this application, reference is made to many blood parameters. Some references that have common shorthand designations are referenced through such shorthand designations. For example, as used herein, HbCO designates carboxyhemoglobin, HbMet designates methemoglobin, and Hbt designates total hemoglobin. Other shorthand designations such as COHb, MetHb, and tHb are also common in the art for these same constituents. These constituents are generally reported herein in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

FIG. 1 illustrates a block diagram of an exemplary embodiment of a patient monitoring system 100. As shown in FIG. 1, the system 100 includes a patient monitor 102 comprising a processing board 104 and a host instrument 108. The processing board 104 communicates with a sensor 106 to receive one or more intensity signal(s) indicative of one or more parameters of tissue of a patient. The processing board 104 also communicates with a host instrument 108 to display determined values calculated using the one or more intensity signals. According to an embodiment, the board 104 comprises processing circuitry arranged on one or more printed circuit boards capable of installation into the monitor 102, or capable of being distributed as some or all of one or more OEM components for a wide variety of host instruments monitoring a wide variety of patient information. In an embodiment, the processing board 102 comprises a sensor interface 110, a digital signal processor and signal extractor ("DSP" or "processor") 112, and an instrument manager 114. In general, the sensor interface 110 converts digital control signals into analog drive signals capable of driving sensor emitters, and converts composite analog intensity signal(s) from light sensitive detectors into digital data.

In an embodiment, the sensor interface 110 manages communication with external computing devices. For example, in an embodiment, a multipurpose sensor port (or input/output port) is capable of connecting to the sensor 106 or alternatively connecting to a computing device, such as a personal computer, a PDA, additional monitoring equipment or networks, or the like. When connected to the computing device, the processing board 104 may upload various stored data for, for example, off-line analysis and diagnosis. The stored data may comprise trend data for any one or more of the measured parameter data, plethysmograph waveform data acoustic sound waveform, or the like. Moreover, the processing board 104 may advantageously download from the computing device various upgrades or executable programs, may perform diagnosis on the hardware or software of the monitor 102. In addition, the processing board 104 may advantageously be used to view and examine patient data, including raw data, at or away from a monitoring site, through data uploads/downloads, or network connections, combinations, or the like, such as for customer support purposes including software maintenance, customer technical support, and the like. Upgradable sensor ports are disclosed in copending U.S. application Ser. No. 10/898,680, filed on Jul. 23, 2004, titled "Multipurpose Sensor Port," incorporated by reference herein.

As shown in FIG. 1, the digital data is output to the DSP 112. According to an embodiment, the DSP 112 comprises a processing device based on the Super Harvard ARChitecture ("SHARC"), such as those commercially available from Analog Devices. However, a skilled artisan will recognize from the disclosure herein that the DSP 112 can comprise a wide variety of data and/or signal processors capable of executing programs for determining physiological parameters from input data. In particular, the DSP 112 includes program instructions capable of receiving multiple channels of data related to one or more intensity signals representative of the absorption (from transmissive or reflective sensor systems) of a plurality of wavelengths of emitted light by body tissue. In an embodiment, the DSP 112 accepts data related to the absorption of eight (8) wavelengths of light, although an artisan will recognize from the disclosure herein that the data can be related to the absorption of two (2) to sixteen (16) or more wavelengths.

FIG. 1 also shows the processing board 104 including the instrument manager 114. According to an embodiment, the instrument manager 114 may comprise one or more microcontrollers controlling system management, including, for example, communications of calculated parameter data and the like to the host instrument 108. The instrument manager 114 may also act as a watchdog circuit by, for example, monitoring the activity of the DSP 112 and resetting it when appropriate.

The sensor 106 may comprise a reusable clip-type sensor, a disposable adhesive-type sensor, a combination sensor having reusable and disposable components, or the like. Moreover, an artisan will recognize from the disclosure herein that the sensor 106 can also comprise mechanical structures, adhesive or other tape structures, Velcro wraps or combination structures specialized for the type of patient, type of monitoring, type of monitor, or the like. In an embodiment, the sensor 106 provides data to the board 104 and vice versa through, for example, a patient cable. An artisan will also recognize from the disclosure herein that such communication can be wireless, over public or private networks or computing systems or devices, or the like.

As shown in FIG. 1, the sensor 106 includes a plurality of emitters 116 irradiating the body tissue 118 with differing wavelengths of light, and one or more detectors 120 capable of detecting the light after attenuation by the tissue 118. In an embodiment, the emitters 116 comprise a matrix of eight (8) emission devices mounted on a flexible substrate, the emission devices being capable of emitting eight (8) differing wavelengths of light. In other embodiments, the emitters 116 may comprise twelve (12) or sixteen (16) emitters, although other numbers of emitters are contemplated, including two (2) or more emitters. As shown in FIG. 1, the sensor 106 may include other electrical components such as, for example, a memory device 122 comprising an EPROM, EEPROM, ROM, RAM, microcontroller, combinations of the same, or the like. In an embodiment, other sensor components may include a temperature determination device 123 or other mechanisms for, for example, determining real-time emission wavelengths of the emitters 116.

The memory 122 may advantageous store some or all of a wide variety data and information, including, for example, information on the type or operation of the sensor 106; type or identification of sensor buyer or distributor or groups of buyer or distributors, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters for which the sensor is capable of supplying sufficient measurement data (e.g., HpCO, HpMet, HbT, or the like), calibration or parameter coefficient data, software such as scripts, executable code, or the like, sensor electronic elements, whether the sensor is a disposable, reusable, multi-site, partially reusable, partially disposable sensor, whether it is an adhesive or non-adhesive sensor, whether the sensor is a reflectance, transmittance, or transreflectance sensor, whether the sensor is a finger, hand, foot, forehead, or ear sensor, whether the sensor is a stereo sensor or a two-headed sensor, sensor life data indicating whether some or all sensor components have expired and should be replaced, encryption information, keys, indexes to keys or hash functions, or the like, monitor or algorithm upgrade instructions or data, some or all of parameter equations, information about the patient, age, sex, medications, and other information that may be useful for the accuracy or alarm settings and sensitivities, trend history, alarm history, or the like. In an embodiment, the monitor may advantageously store data on the memory device, including, for example, measured trending data for any number of parameters for any number of patients, or the like, sensor use or expiration calculations, sensor history, or the like.

FIG. 1 also shows the patient monitor 102 including the host instrument 108. In an embodiment, the host instrument 108 communicates with the board 104 to receive signals indicative of the physiological parameter information calculated by the DSP 112. The host instrument 108 preferably includes one or more display devices 124 capable of displaying indicia representative of the calculated physiological parameters of the tissue 118 at the measurement site. In an embodiment, the host instrument 108 may advantageously comprise a handheld housing capable of displaying one or more of a pulse rate, plethysmograph data, perfusion quality such as a perfusion quality index ("PI™"), signal or measurement quality ("SQ"), values of blood constituents in body tissue, including for example, $SpO_2$, HbCO, HbMet, Hbt, or the like. In other embodiments, the host instrument 108 is capable of displaying values for one or more of Hbt, Hb, blood glucose, bilirubin, or the like. The host instrument 108 may be capable of storing or displaying historical or trending data related to one or more of the measured values, combinations of the measured values, plethysmograph data, or the like. The host instrument 108 also includes an audio indicator 126 and user input device 128, such as, for example, a keypad, touch screen, pointing device, voice recognition device, or the like.

In still additional embodiments, the host instrument 108 includes audio or visual alarms that alert caregivers that one or more physiological parameters are falling below predetermined safe thresholds. The host instrument 108 may include indications of the confidence a caregiver should have in the displayed data. In a further embodiment, the host instrument 108 may advantageously include circuitry capable of determining the expiration or overuse of components of the sensor 106, including, for example, reusable elements, disposable elements, or combinations of the same.

Although described in terms of certain embodiments, other embodiments or combination of embodiments will be apparent to those of ordinary skill in the art from the disclosure herein. For example, the monitor 102 may comprise one or more monitoring systems monitoring parameters, such as, for example, vital signs, blood pressure, ECG or EKG, respiration, glucose, bilirubin, or the like. Such systems may combine other information with intensity-derived information to influence diagnosis or device operation. Moreover, the monitor 102 may advantageously include an audio system, preferably comprising a high quality audio processor and high quality speakers to provide for voiced alarms, messaging, or the like. In an embodiment, the monitor 102 may advantageously include an audio out jack, conventional audio jacks, headphone jacks, or the like, such that any of the display information disclosed herein may be audiblized for a listener. For example, the monitor 102 may include an audible transducer input (such as a microphone, piezoelectric sensor, or the like) for collecting one or more of heart sounds, lung sounds, trachea sounds, or other body sounds and such sounds may be reproduced through the audio system and output from the monitor 102. Also, wired or wireless communications (such as Bluetooth or WiFi, including IEEE 801.11a, b, or g), mobile communications, combinations of the same, or the like, may be used to transmit the audio output to other audio transducers separate from the monitor 102.

For example, patterns or changes in the continuous noninvasive monitoring of intensity-derived information may cause the activation of other vital sign measurement devices, such as, for example, blood pressure cuffs.

Figure 2:
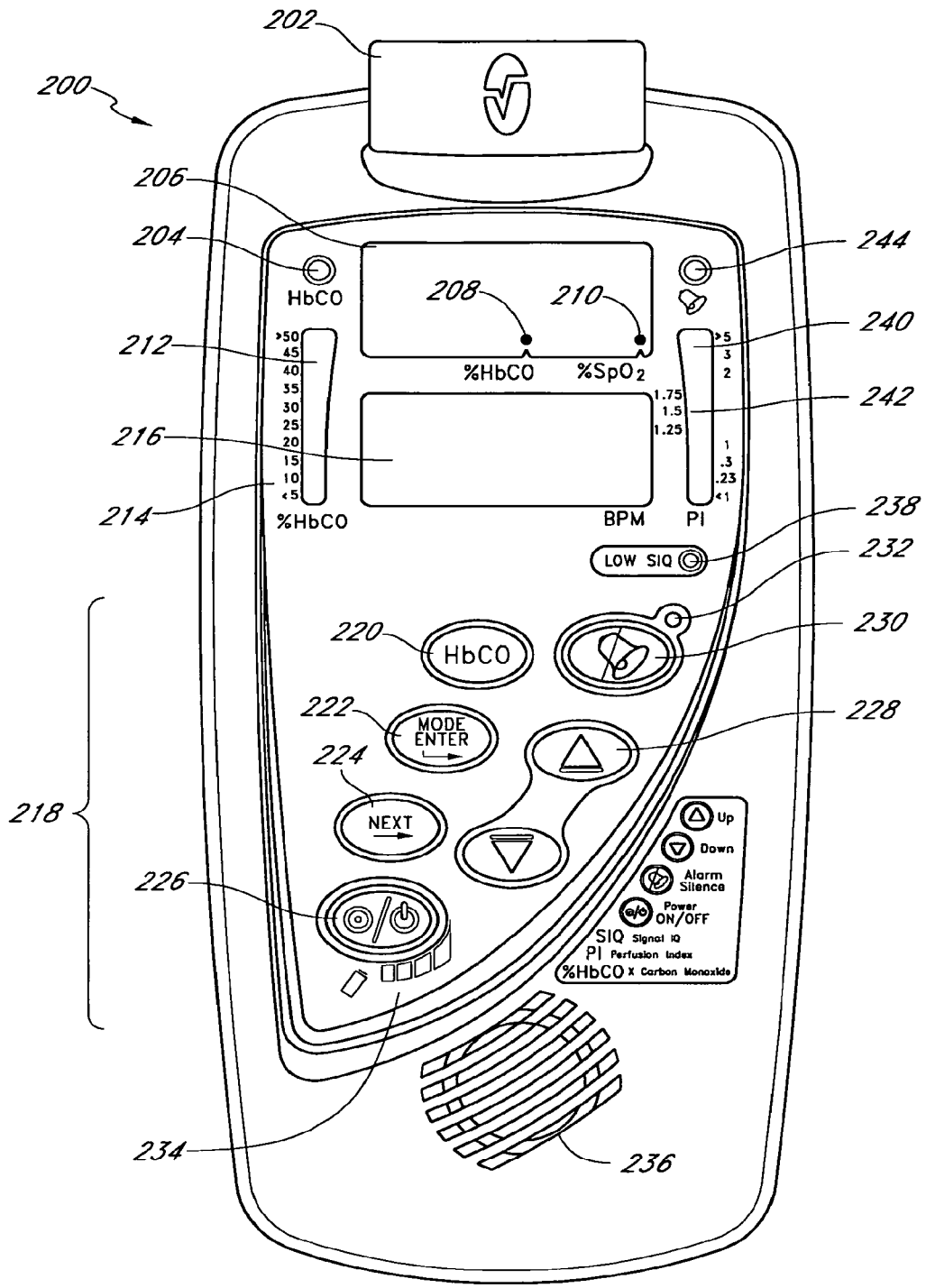
FIG. 2 illustrates a top elevation view of an exemplary handheld noninvasive multi-parameter patient monitor capable of displaying at least HbCO, such as, for example, the patient monitor of FIG. 1.

FIG. 2 illustrates a perspective view of an exemplary handheld noninvasive multi-parameter patient monitor 200, such as, for example, the patient monitor 102 of FIG. 2. Patient monitors 200 exhibiting combinations of many of the features described herein are advantageously commercially available from Masimo under the brand name "Rad 57c." As shown in FIG. 1, the monitor 200 includes a patient cable connector 202 capable of mechanical mating with a patient cable to establish communication between the board 104 and the sensor 106. In an embodiment, the connector 202 comprises a multipurpose cable connector such as that disclosed in the incorporated U.S. application Ser. No. 10/898,680, titled "Multipurpose Sensor Port," disclosing communication between the board 104 and an external computing device.

The monitor 200 also comprises a HbCO indicator 204 advantageously providing a visual queue that a HbCO capable sensor is properly connected through the connector 202. For example, the HbCO indicator 204 may advantageously activate when a sensor is connected that communicates sufficient information to determine HbCO, such as, for example, a sensor capable of emitting sufficient different wavelengths of light, a sensor storing sufficient data on the memory 122, a sensor having appropriate encryption data or key, combinations of the same, or the like. For example, in an embodiment, the processor 112 may receive information from a memory 122 indicating a number of available LED wavelengths for the attached sensor. Based on the number of wavelengths, or other information stored on the memory 122, the processor 112 may determine whether an HbCO-ready sensor has been attached to the monitor 200. An artisan will also recognize from the disclosure herein that the HbCO indicator 204 may advantageously comprise a HbMet indicator, Hbt indicator, or the like, which activates to a predetermined color associated with a parameter, or any color, or deactivates the same, to convey a type of attached sensor. Moreover, the artisan will recognize from the disclosure herein other parameters that may use other sensor components and the monitor 200 may include indicators capable of indicating communication with those types of sensors.

In an embodiment, the monitor 200 may also audibly indicate the type of sensor connected. For example, the monitor 200 may emit predetermined number or frequency of beeps associated with recognition of a particular sensor, a particular manufacturer, failure to recognize the sensor, or the like. Moreover, the sensor type may be indicative of the componentry, such as, for example, whether the sensor produces sufficient data for the determination of HbCO, HbMet, Hbt and $SpO_2$, $SpO_2$ only, $SpO_2$ and HbMet, any combination of the foregoing or other parameters, or the like. Additionally, the sensor type may be indicative of specific sensors designed for a type of patient, type of patient tissue, or the like. In other embodiments, the monitor 200 may announce the type of connector through speaker 236.

An artisan will also recognize from the disclosure herein that other mechanical (such as keys), electrical, or combination devices may inform the monitor 202 of the type of attached sensor. In an embodiment, the processor 112 also may select to drive less emitters that are currently available, such as, for example, in the presence of low noise and when power consumption is an issue.

The monitor 200 also comprises a multi-mode display 206 capable of displaying, for example, measurements of $SpO_2$ and HbCO (or alternatively, HbMet). In an embodiment, the display 206 has insufficient space or display real estate to display the many parameters capable of being measured by the monitor 200. Thus, the multi-mode display 206 may advantageously cycle through two or more measured parameters in an area common to both parameters even when shifted. In such embodiments, the monitor 200 may also advantageously include parameter indicators 208, 210, providing additional visual queues as to which parameter is currently displayed. In an embodiment, the display may also cycle colors, flash rates, or other audio or visual queues providing readily identifiable information as to which measured parameter is displayed. For example, when the multi-mode display 206 displays measured values of $SpO_2$ that are normal, the numbers may advantageously appear in green, while normal measured values of HbCO may advantageously appear in orange, and normal measured values of HbMet may appear in blue. Moreover, in an embodiment, the display 206 flashes at a predefined rate when searching for saturation and at another predefined rate when a signal quality is below a predetermined threshold.

The monitor 200 also comprises a HbCO bar 212 where in an embodiment a plurality of LED's activate from a bottom toward a top such that the bar "fills" to a level proportional to the measured value. For example, the bar 212 is lowest when the dangers from carbon monoxide poisoning are the least, and highest when the dangers are the greatest. The bar 212 includes indicia 214 that provide an indication of the severity of carbon monoxide saturation in a patient's blood. As shown in FIG. 2, the bar 212 and the indicia 214 continuously indicate the concentration of HbCO in about 5% increments. The indicia 214 indicate a measurement of HbCO saturation percentage between about 0 and about 50% with a granularity of about 5%. However, an artisan will also recognize from the disclosure herein a wide variety of ranges and granularities could be used, the indicia 214 could be electronically displayed in order to straightforwardly increase or decrease resolution, or the like. For example, HbCO may advantageously be displayed with greater resolution than ±about %5 in a lower portion of the scale. For example, an HbCO bar may advantageously include a scale of about <3%, about 6%, about 9%, about 12%, about 15%, about 20%, about 25%, about 30%, about 35%, and about >40%.

As is known in the art, carbon monoxide in the blood can lead to serious medical issues. For example and depending upon the particular physiology of a patient, about 10% carbon monoxide saturation can lead to headaches, about 20% can lead to throbbing headaches, or dyspnea on exertion, about 30% can lead to impaired judgment, nausea, dizziness and/or vomiting, visual disturbance, or fatigue, about 40% can lead to confusion and syncope, and about 50% and above can lead to comas, seizures, respiratory failure and even death.

In an embodiment, the bar 212 is the same or similar color as the multi-mode display 206 when displaying HbCO. In other embodiments, the bar 212 is lowest and green when the dangers from carbon monoxide poisoning are the least, and highest and red when the dangers are the greatest. In an embodiment, as HbCO increases, the entire bar 212 may advantageously change color, such as, for example, from green to red, to provide a clear indication of deepening severity of the condition. In other embodiments, the bar 212 may advantageously blink or flash, an audio alarm may beep or provide a continuation or rise in pitch or volume, or the like to alert a caregiver of deepening severity. Moreover, straightforward to complex alarm rules may be implemented to reduce false alarms based on, for example, knowledge of the physiological limitations on the rate of change in HbCO or the like.

Additionally, the monitor 200 may be capable of storing and outputting historical parameter data, display trend traces or data, or the like. Although the foregoing bar 212 has been described in terms of certain preferred embodiments, other embodiments will be apparent to those of ordinary skill in the art from the disclosure herein.

FIG. 2 also shows the monitor 200 including a pulse display 216 displaying measured pulse rate in beats per minute ("BPM"). In an embodiment, the display 212 flashes when searching for a pulse. The pulse display 216 advantageously displays measured pulse rates from about zero (0) to about two hundred and forty (240) BPM. Moreover, when the measured pulse rates are considered normal, the pulse display 216 is advantageously green. Similar to other displays associated with the monitor 200, the pulse display 216 may employ a variety of color changes, audio alarms, or combinations of the same to indicate measured BPM below predetermined safe thresholds. In an embodiment, the pulse rate display 216 displays the measured pulse rate during the display of $SpO_2$ and displays message data during the display of other parameters. For example, during the display of HbCO, the display 216 may advantageously display the term "CO." In an embodiment, the display of the message data may be in the same or similar color as the other displays. For example, in an embodiment, the multi-mode display 206, the bar 212, and the pulse display 216 may all display data or messages in orange when the multi-mode display 206 displays measured HbCO values.

FIG. 2 also illustrates the monitor 200 comprising user input keys 218, including a HbCO button 220, mode/enter button 222, next button 224, power on/off button 226, up/down button 228, and alarm silence button 230. In an embodiment, activation of the HbCO button 220 toggles the measured value displayed in the multi-mode display 206. For example, activation of the HbCO button 220 toggles the multi-mode display 206 from displaying measured values of $SpO_2$ to HbCO for about ten (10) seconds. Activation of the mode/enter button 222 or the next button 224 during the ten (10) second period returns the multi-mode display 206 back to $SpO_2$. A skilled artisan will also recognize that activation of the HbCO button 220 may advantageously toggle through a plurality of measured values, and that such values may be displayed for short segments and then return to $SpO_2$, may remain displayed until further activation of the button 220, or the like.

Activation of the mode/enter button 222 cycles through various setup menus allowing a caregiver to select or activate certain entries within the menu setup system, including alarm threshold customizations, or the like. Activation of the next button 224 can move through setup options within the menu setup system and in an embodiment is not active during normal patient monitoring. For example, a caregiver may activate the mode/enter button 222 and the next button 224 to specify high and low alarm thresholds for one or more of the measured parameters, to specify device sensitivity, trend settings, display customizations, color code parameters, or the like. In an embodiment, the high alarm setting for $SpO_2$ can range from about two percent (2%) to about one hundred percent (100%) with a granularity of about one percent (1%). The low alarm setting for $SpO_2$ can range from about one percent (1%) to about one hundred percent (100%) with a granularity of about one percent (1%). Moreover, the high alarm setting for pulse rate can range from about thirty (30) BPM to about two hundred and forty (240) BPM with a granularity of about five (5) BPM. The low alarm setting for pulse rate can range from about twenty five (25) BPM to about two hundred and thirty five (235) BPM with a granularity of about five (5) BPM. Other high and low ranges for other measured parameters will be apparent to one of ordinary skill in the art from the disclosure herein.

In a further embodiment, a caregiver may activate the mode/enter button 222 and the next button 224 to specify device sensitivity, such as, for example, device averaging times, probe off detection, whether to enable fast saturation calculations, or the like. Various embodiments of fast saturation calculations are disclosed in U.S. patent application Ser. No. 10/213,270, filed Aug. 5, 2002, titled "Variable Indication Estimator" and incorporated by reference herein. Using the menus, a caregiver may also advantageously enter appropriate information governing trend collection on one or more of the measured parameters, input signals, or the like.

FIG. 2 also shows the power on/off button 226. Activation of the power on/off button 226 activates and deactivates the monitor 200. In an embodiment, press-and-hold activation for about two (2) seconds shuts the monitor 200 off. In an additional embodiment, activation of the on/off button 226 advantageously initiates detection of a type of attached sensor. For example, activation of the on/off button 226 may advantageously cause the monitor 200 to read information from a memory on an attached sensor and determine whether sufficient wavelengths exist on the sensor to determine one or more the physiological parameters discussed in the foregoing.

An artisan will recognize from the disclosure herein that the on/off button 226 may advantageously cause an electronic determination of whether to operate in at powers consisted with the U.S. (60 Hz) or another nationality (50 Hz). In an embodiment, such automatic determination and switching is removed from the monitor 200 in order to reduce a likelihood of problematic interfering crosstalk caused by such power switching devices.

Activation of the up/down button 228 may advantageously adjust the volume of the pulse beep tone. Additionally, activation of the up/down button 228 within the menu setup system, causes the selection of values with various menu options.

Moreover, activation of the alarm silence button 230 temporarily silences audio alarms for a predetermined period, such as, for example, about one hundred and twenty (120) seconds. A second activation of the alarm silence button 230 mutes (suspends) the alarm indefinitely, while a third activation returns the monitor 200 to standard alarm monitoring. FIG. 2 also shows the alarm silence button 230 includes an alarm silenced indicator 232. The alarm silenced indicator 232 may advantageously flash to indicate one or more alarms are temporarily silenced, may illuminate solid to indicate the alarms have been muted, or the like. Moreover, an artisan will recognize from the disclosure herein a wide variety of alarm silencing methodologies.

The monitor 200 also includes a battery level indicator 234 indicating remaining battery life. In the illustrated embodiment, four LED's indicate the status of the battery by incrementally deactivating to indicate proportionally decreasing battery life. In an embodiment, the four LED's may also change color as the battery charge decreases, and the final LED may begin to flash to indicate that the caregiver should replace the batteries.

FIG. 2 also shows the monitor 200 including an audio transducer or speaker 236. The speaker 236 advantageously provides audible indications of alarm conditions, pulse tone and feedback for key-presses, or the like. Moreover, the monitor 202 includes a low signal quality indicator ("SO" or "SIQ™") 238. The signal IQ indicator 238 activates to inform a caregiver that a measured value of the quality of the incoming signal is below predetermined threshold values. For example, in an embodiment, the measured value for signal IQ is at least partially based on an evaluation of the plethysmograph data's correspondence to predetermined models or characteristics of physiological signals. In an embodiment, the signal IQ indicator 238 output may be associated with the displayed parameter. For example, the output may be associated with one threshold for the display of $SpO_2$ and another for the display of other parameter data.

The monitor 200 also comprises a perfusion quality index ("PI™") bar 240 (which quantifies the measure of perfusion of the patient) where in an embodiment a plurality of LED's activate from a bottom toward a top such that the bar "fills" to a level proportional to the measured value. In one embodiment, the PI™ bar 240 shows a static value of perfusion for a given time period, such as, for example, one or more pulses. In another embodiment, or functional setting, the PI™ bar 240 may advantageously pulse with a pulse rate, may hold the last reading and optionally fade until the next reading, may indicate historical readings through colors or fades, or the like. Additionally, the PI™ bar 240 may advantageously change colors, flash, increasingly flash, or the like to indicate worsening measured values of perfusion.

The PI™ bar 240 can be used to simply indicate inappropriate occlusion due, for example, to improper attachment of the sensor 106. The PI™ bar 240 can also be used as a diagnostic tool during low perfusion for the accurate prediction of illness severity, especially in neonates. Moreover, the rate of change in the PI™ bar 240 can be indicative of blood loss, sleep arousal, sever hypertension, pain management, the presence or absence of drugs, or the like. According to one embodiment, the PI™ bar 240 values may comprise a measurement of the signal strength of the arterial pulse as a percentage of the total signal received. For example, in one preferred embodiment, the alternating portion of at least one intensity signal from the sensor 106 may advantageously be divided by the static portion of the signal. For example, an infrared intensity signal may advantageously be used as it is less subjective to noise.

In an embodiment, a measurement below about 1.25% may indicate medical situations in need of caregiver attention, specifically in monitored neonates. Because of the relevance of about 1.25%, the PI™ bar 240 may advantageously include level indicia 242 where the indicia 242 swap sides of the PI™ bar 240, thus highlighting any readings below about that threshold. Moreover, behavior of the PI™ bar 240, as discussed above, may advantageously draw attention to monitored values below such a threshold.

As discussed above, the monitor 200 may include output functionality that outputs, for example, trend perfusion data, such that a caregiver can monitor measured values of perfusion over time. Alternatively or additionally, the monitor 200 may display historical trace data on an appropriate display indicating the measured values of perfusion over time. In an embodiment, the trend data is uploaded to an external computing device through, for example, the multipurpose sensor connector 202 or other input output systems such as USB, serial or parallel ports or the like.

The monitor 200 also includes an alarm indicator 244 capable of providing visual queues of the status of one or more of the measured parameters. For example, the alarm indicator 244 may advantageously be green when all of the measured parameters are within normal conditions, may gradually fade to red, may flash, increasing flash, or the like, as one or more of the measured values approaches or passes predetermined thresholds. In an embodiment, the alarm indicator 244 activates when any parameter falls below an associated threshold, thereby advantageously informing a caregiver that perhaps a nondisplayed parameters is at an alarm condition. In another embodiment, the alarm indicator 244 may indicate the status of the parameter displayed on the multi-mode display 206. In an embodiment, the speaker 236 may sound in conjunction with and/or in addition to the indicator 244. Moreover, in an embodiment, an alarming parameter may automatically be displayed, may be emphasized, flashed, colored, combinations of the same or the like to draw a user's attention to the alarming parameter.

Although the foregoing invention has been described in terms of certain preferred embodiments, other embodiments will be apparent to those of ordinary skill in the art from the disclosure herein.

Figure 3:
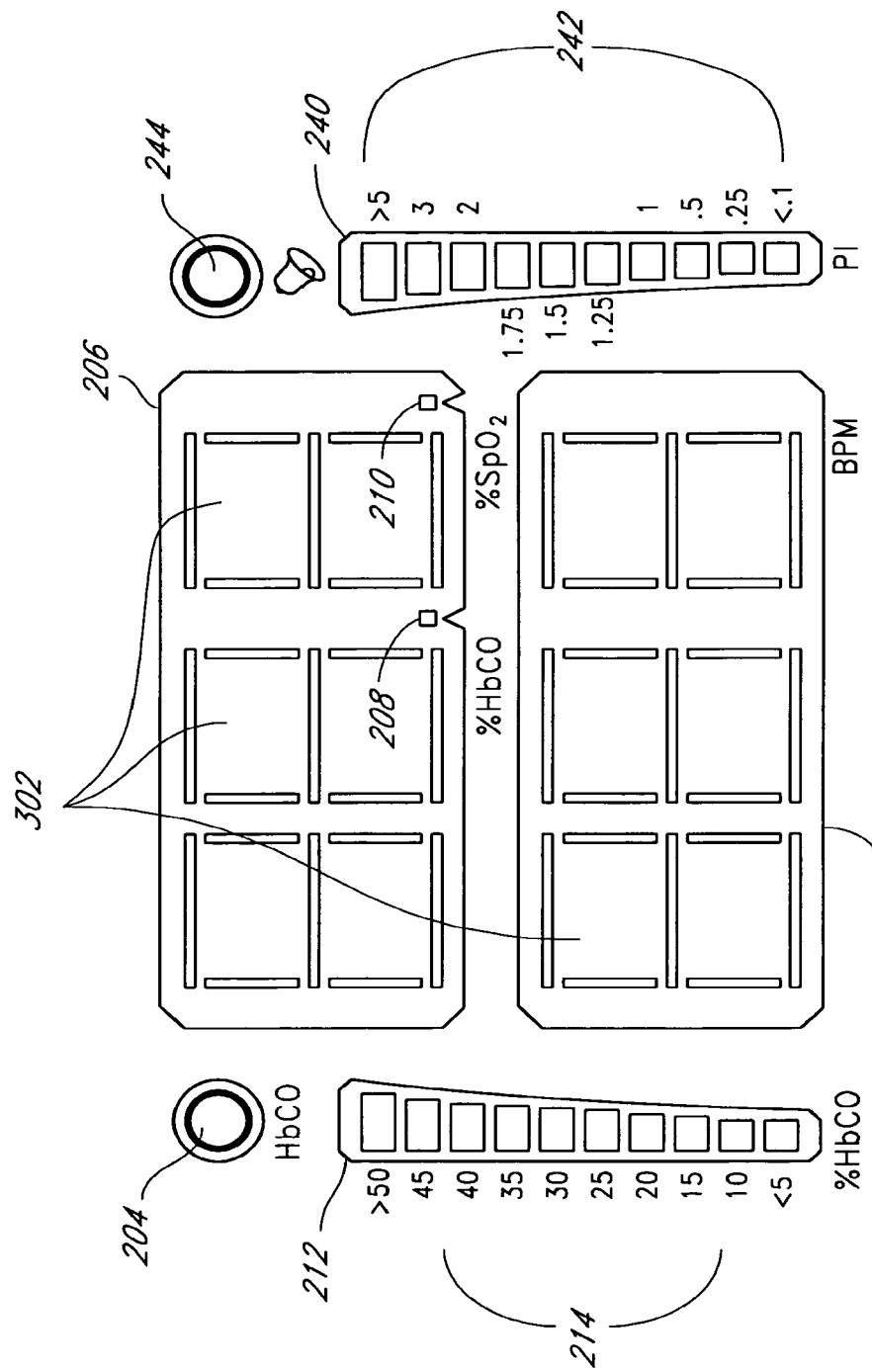
FIG. 3 illustrates an exemplary display of the patient monitor of FIG. 2.

FIG. 3 illustrates an exemplary display of the patient monitor 200. As shown in FIG. 3, the display includes the multi-mode display 206, the pulse rate display 216, parameter indicators 208, 210, the HbCO bar 212 and indicator 204, the PI™ bar 240, and the alarm indicator 244. In an embodiment, the multi-mode display 206 and the pulse rate display 216 each comprise a plurality of seven segment displays 302 capable of displaying alpha-numeric information. As disclosed in the foregoing, the exemplary display may advantageously include color-coded parameter displays. Moreover, the exemplary display may include color progressions, flashing, flashing progressions, audible alarms, audible progressions, or the like, indicating worsening measured values of physiological data. In addition, in an embodiment, some or all of the displays may flash at a first rate to indicate attempts to acquire data when actual measured values are unavailable. Moreover, some or all of the display may flash at a second rate to indicate low signal quality where confidence is decreasing that the measured values reflect actual physiological conditions.

Figure 4:
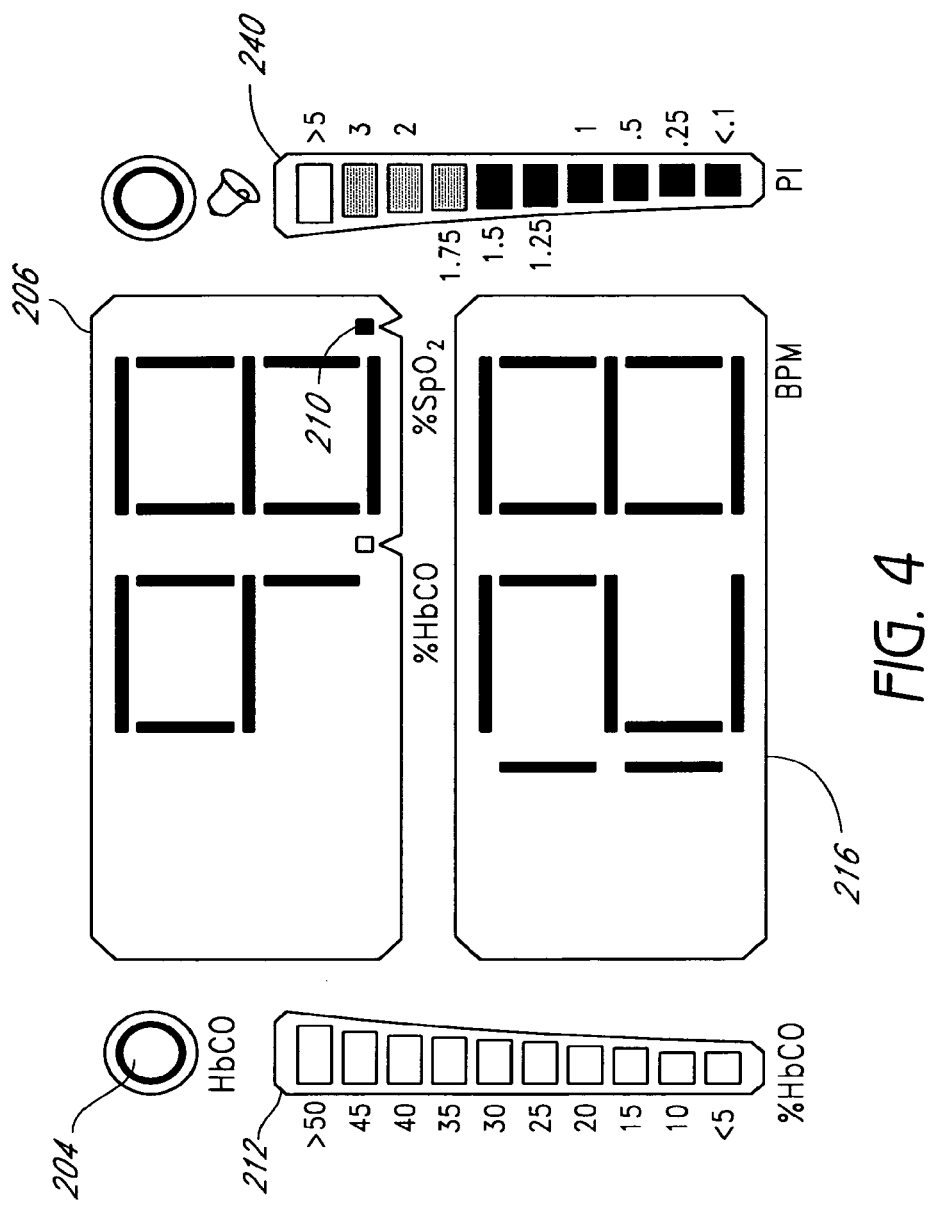
FIG. 4 illustrates the display of FIG. 3 showing measured values of $SpO_2$, BPM, perfusion, and type of sensor according to an exemplary embodiment of the patient monitor of FIG. 1.

FIG. 4 illustrates the display of FIG. 3 showing measured values of SpO$_2$, BPM, perfusion, and type of sensor, according to an exemplary embodiment of the patient monitor of FIG. 1. As shown in FIG. 4, the multi-mode display 206 is displaying a percentage value of SpO$_2$, and the pulse rate display 216 is displaying a pulse rate in beats per minute. Accordingly, the parameter indicator 210 is activated to confirm the display of measured values of SpO$_2$. As disclosed in the foregoing, in an embodiment, the multi-mode display 206 is red, indicating blood oxygen measurements while the pulse rate display 216 is green, indicating normal values of a patient's pulse.

FIG. 4 also shows the PI™ bar 240 almost fully activated, representing good perfusion. In addition, the HbCO indicator 204 is showing communication with a sensor producing insufficient data to determine measured values of additional parameters, such as, HbCO. In an embodiment, such sensors may comprise sensors capable of emitting light at about two (2) different wavelengths, may comprise sensors with insufficient data stored on a memory associated therewith, or the like.

Figure 5:
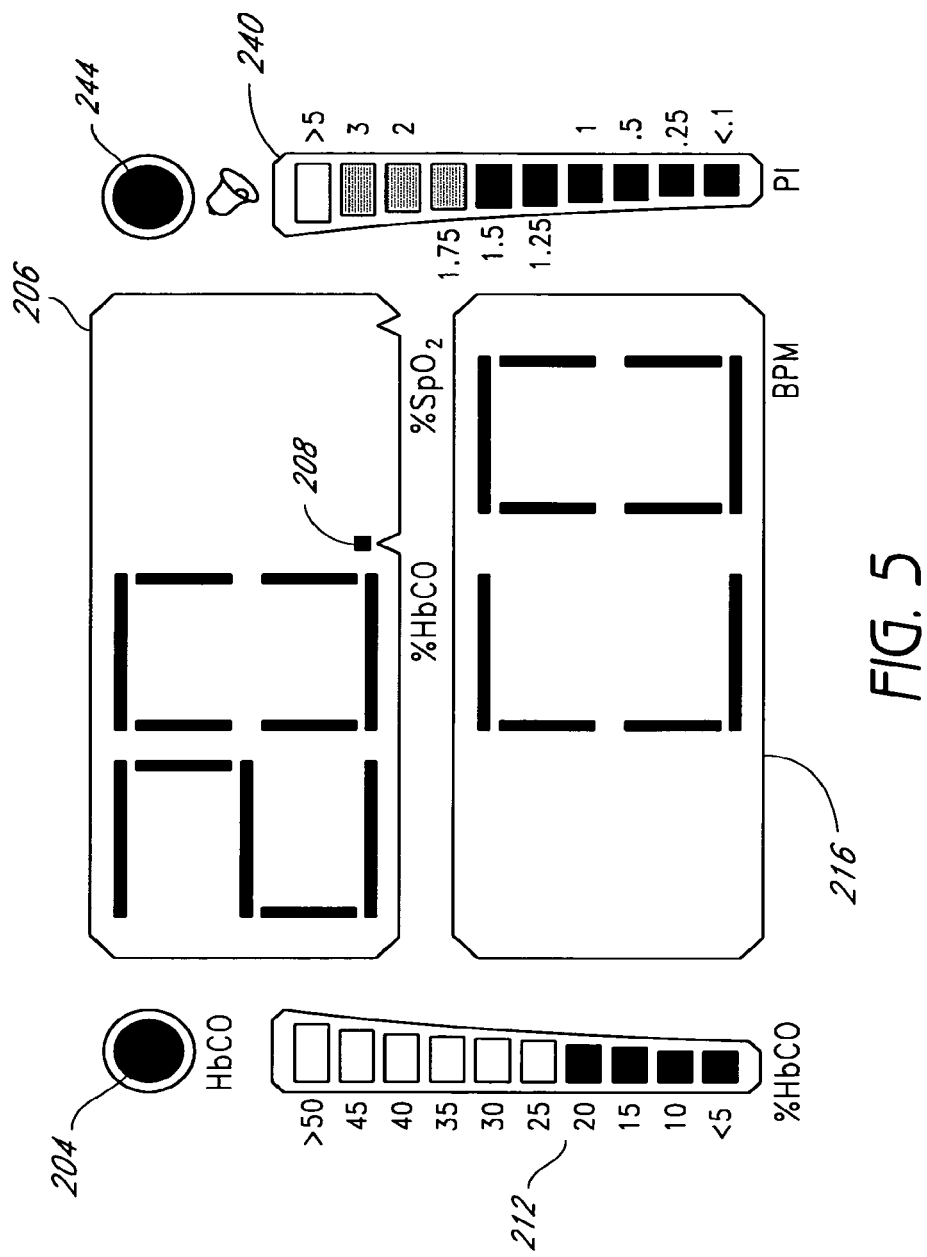
FIG. 5 illustrates the display of FIG. 3 showing measured values of HbCO, perfusion, and type of sensor according to an exemplary embodiment of the patient monitor of FIG. 1.

FIG. 5 illustrates the display of FIG. 3 showing measured values of HbCO, perfusion, and type of sensor, according to an exemplary embodiment of the patient monitor of FIG. 1. As shown in FIG. 5, the multi-mode display 206 is displaying a percentage value of HbCO, and the pulse rate display 216 is displaying an appropriate message indicating the HbCO measurement, such as, for example, "CO". Also, the multi-mode display 206 has shifted the data to the left to quickly and efficiently indicate that the displayed parameter is other than SpO$_2$. Accordingly, the parameter indicator 208 is also activated to confirm the display of measured values of HbCO. As disclosed in the foregoing, in an embodiment, the multi-mode display 206 and pulse rate display message 216 are orange.

FIG. 5 also shows the PI™ bar 240 almost fully activated, representing good perfusion. In addition, the activation of the HbCO indicator 204 represents communication with a sensor capable of producing sufficient data to determine measured values of HbCO. In an embodiment, such sensors may comprise sensors capable of emitting light at about eight (8) or more different wavelengths; however, such sensors may comprise about two (2) or more different wavelengths. Moreover, such sensors may have appropriate data stored on a memory associated therewith, or the like. FIG. 5 also shows the HbCO measurement being about 20% (as illustrated on the HbCO bar 212 and multi-mode display 206) thereby indicating a potentially dangerous situation that if exacerbated, will become quite problematic. Therefore, the alarm indicator 244 is also activated, and in some embodiments, the speaker 236 as well.

Figure 6:
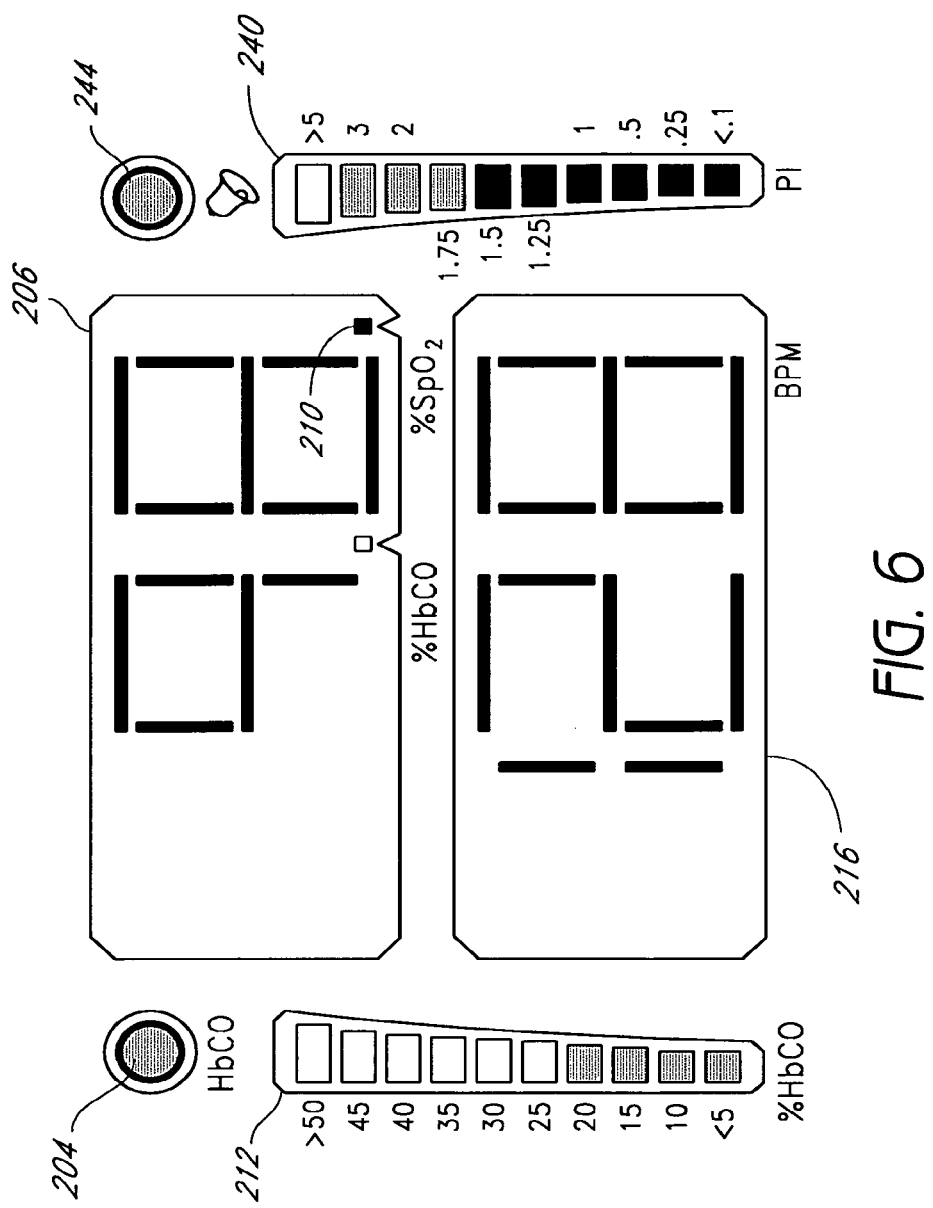
FIG. 6 illustrates the display of FIG. 3 showing measured values of $SpO_2$, HbCO, BPM, perfusion, and type of sensor, according to an exemplary embodiment of the patient monitor of FIG. 1.

FIG. 6 illustrates the display of FIG. 3 showing measured values of SpO$_2$, HbCO, BPM, perfusion, and type of sensor, according to an exemplary embodiment of the patient monitor of FIG. 1. In contrast to FIG. 4, FIG. 6 shows that the monitor 200 is communicating with a sensor capable of producing sufficient data to determine measured values of HbCO, even though the displayed values are that of SpO$_2$ and BPM. Thus, FIG. 6 shows the activation of the HbCO indicator 204, and the continuous monitoring of HbCO by the HbCO bar 212. FIG. 6 also shows a high value of HbCO, and therefore, the indication of an alarm condition by activation of the alarm indicator 244. In an embodiment, upon determination of an alarm condition on a nondisplayed parameter, the monitor 200 may advantageously provide an alarm indication through speaker and alarm indicator activation, automatic toggle to the nondisplayed parameter on the multi-mode display 206 for a defined or undefined time, or the like.

Figure 7:
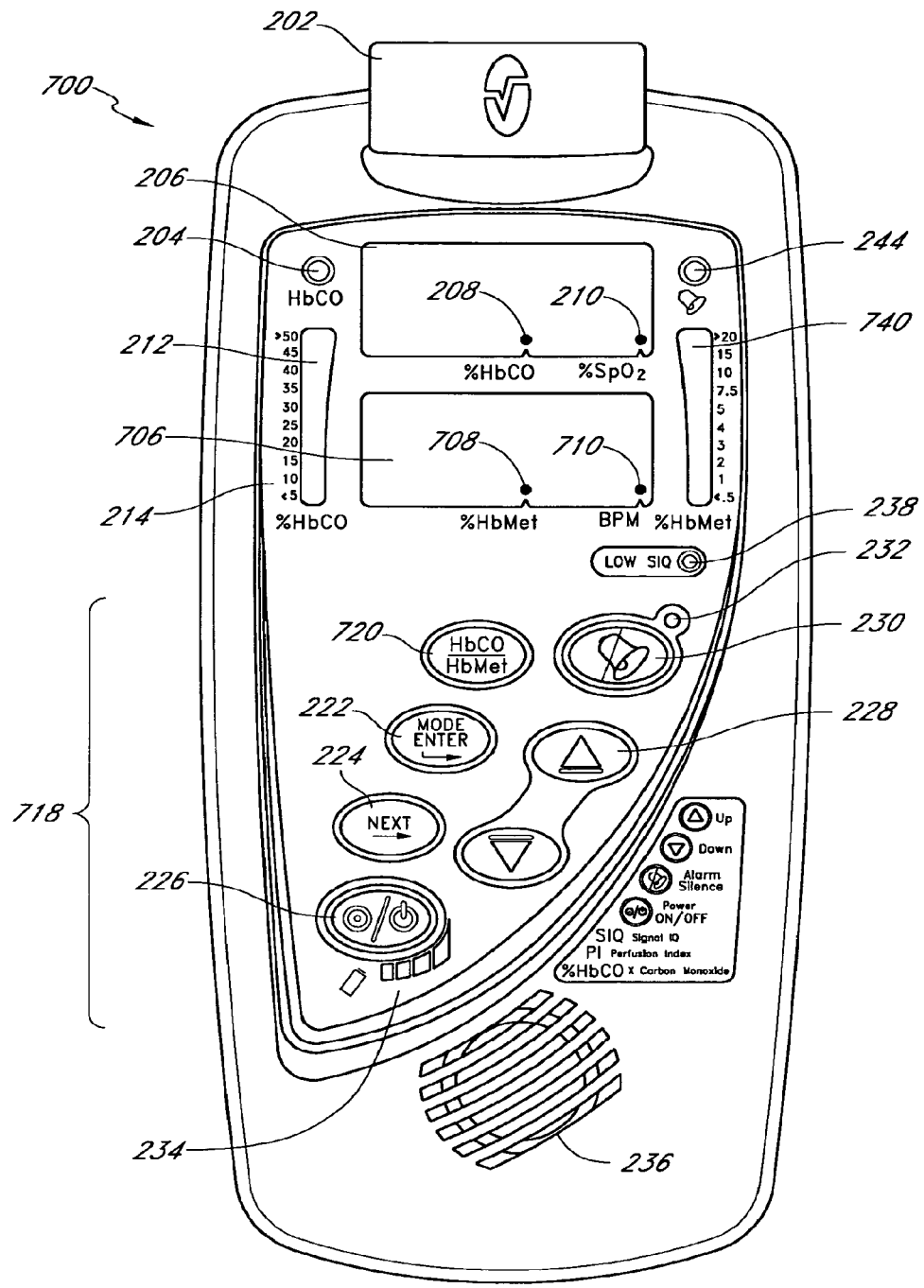
FIG. 7 illustrates a top elevation view of an exemplary handheld noninvasive multi-parameter patient monitor capable of displaying at least HbCO and HbMet, such as, for example, the patient monitor of FIG. 1.

FIG. 7 illustrates a top elevation view of an exemplary handheld noninvasive multi-parameter patient monitor 700 capable of displaying at least HbCO and HbMet, such as, for example, the patient monitor of FIG. 1. Patient monitors exhibiting combinations of many of the features described herein are advantageously commercially available from Masimo under the brand name "Rad 57 cm." As shown in FIG. 7, the monitor 700 comprises a monitor similar to monitor 200 disclosed with reference to FIG. 2. Moreover, monitor 700 further includes a multi-mode display 706 capable of displaying, for example, measurements of HbMet and BPM. In an embodiment, the display 706 has insufficient space or display real estate to display the many parameters capable of being measured by the monitor 700. Thus, the multi-mode display 706 may advantageously cycle through two or more measured parameters. In such embodiments, the monitor 700 may also advantageously include parameter indicators 708, 710, providing additional visual queues as to which parameter is currently displayed. In an embodiment, the display 706 may also cycle colors, flash rates, or other audio or visual queues providing readily identifiable information as to which measured parameter is displayed. For example, when the multi-mode display 706 displays measured values of BPM that are normal, the numbers may advantageously appear in green, while normal measured values of HbMet may appear in blue. Moreover, in an embodiment, the display 706 may flash at a predefined rate when searching for saturation and at another predefined rate when a signal quality is below a predetermined threshold.

FIG. 7 also illustrates the monitor 700 comprising user input keys 718, including an HbCO/HbMet button 220. In an embodiment, activation of the HbCO/HbMet button 720 toggles the measured value displayed in the multi-mode display 706. For example, activation of the HbCO/HbMet button 720 toggles the multi-mode display 206 from displaying measured values of SpO$_2$ and BPM, to HbCO and HbMet for about ten (10) seconds. Activation of the mode/enter button 222 or the next button 224 during the ten (10) second period returns the multi-mode display 706 back to SpO$_2$ and BPM. A skilled artisan will also recognize that activation of the HbCO/HbMet button 720 may advantageously toggle through a plurality of measured values, and that such values may be displayed for short segments and then return to SpO$_2$ and BPM, may remain displayed until further activation of the button 720, or the like.

The monitor 700 also comprises a coarser indication of HbMet through an HbMet bar 740. In an embodiment, a plurality of LED's activate from a bottom toward a top such that the bar "fills" to a level proportional to the measured value, with increments at about 0.5%, about 1%, about 2%, about 3%, about 4%, about 5%, about 7.5%, about 10%, about 15% and greater than about 20%, although an artisan will recognize from the disclosure herein other useful delineations. Additionally, the HbMet bar 740 may advantageously change colors, flash, increasingly flash, or the like to indicate worsening measured values of perfusion.

Although disclosed with reference to the HbMet bar 740, and artisan will recognize from the disclosure herein other coarse or even gross indications of HbMet, or any measured parameter. For example, a single LED may advantageously show green, yellow, and red, to indicate worsening coarse values of HbMet. Alternatively, a single LED may simply light to indicate an alarm or approaching alarm condition.

Figure 8:
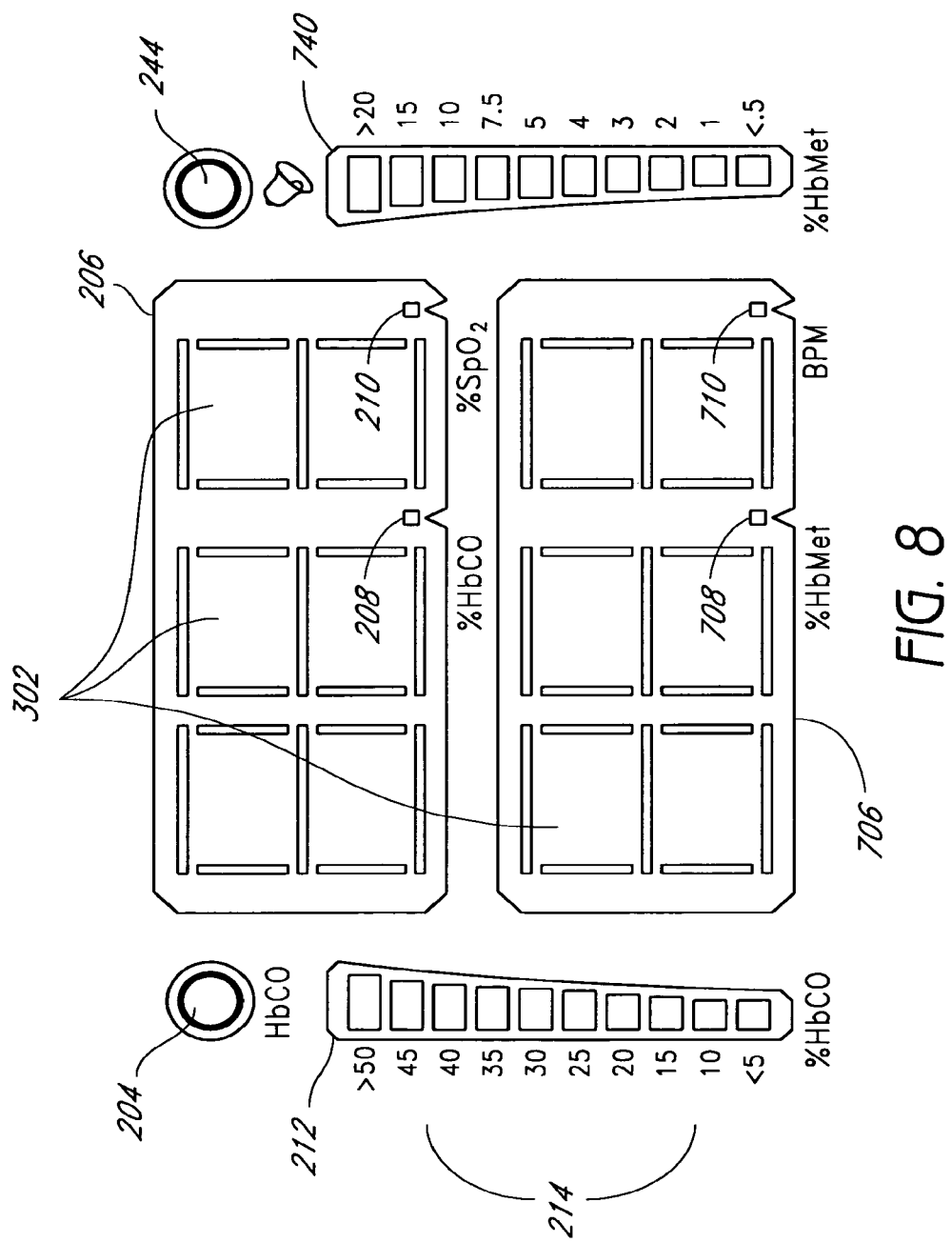
FIG. 8 illustrates an exemplary display of the patient monitor of FIG. 7.

FIG. 8 illustrates an exemplary display of the patient monitor 700 of FIG. 7. As shown in FIG. 8, the display includes the multi-mode displays 206, 706, parameter indicators 208, 210, 708, 710, the HbCO bar 212 and indicator 204, the HbMet bar 740, and the alarm indicator 244. In an embodiment, the multi-mode display 706 is similar to multi-mode display 206, comprising a plurality of seven segment displays 302 capable of displaying alpha-numeric information, and capable of altering its display characteristics or aspects in a wide variety of configurations discussed with reference to the display 206.

Figure 9:
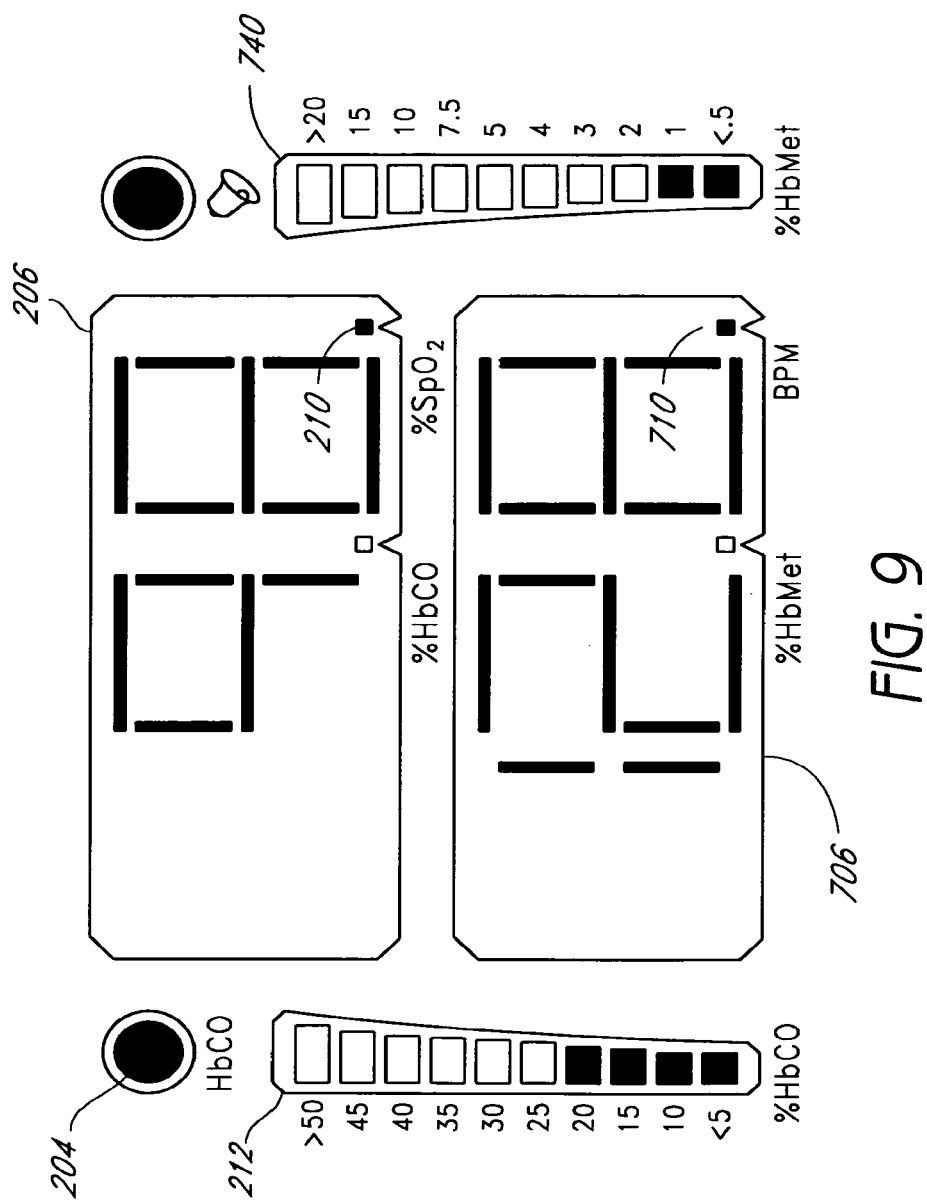
FIG. 9 illustrates the display of FIG. 8 showing measured values of $SpO_2$, BPM, HbCO, HbMet, and type of sensor according to an exemplary embodiment of the patient monitor of FIG. 1.

FIG. 9 illustrates the display of FIG. 8 showing measured values of SpO$_2$, BPM, HbCO, HbMet, and type of sensor according to an exemplary embodiment of the patient monitor of FIG. 1. FIG. 9 also shows the HbMet bar 740 near the bottom and corresponding to about 1%, representing acceptable HbMet, while the HbCO bar 212 hovers at a dangerous near 20%. In addition, the HbCO indicator 204 is showing communication with a sensor producing sufficient data to determine measured values of additional parameters, such as, HbMet, HbCO or the like. In an embodiment, such sensors may comprise sensors capable of emitting light of more than two (2) different wavelengths, preferably more than four (4) different wavelengths, and more preferably eight (8) or more different wavelengths.

Figure 10:
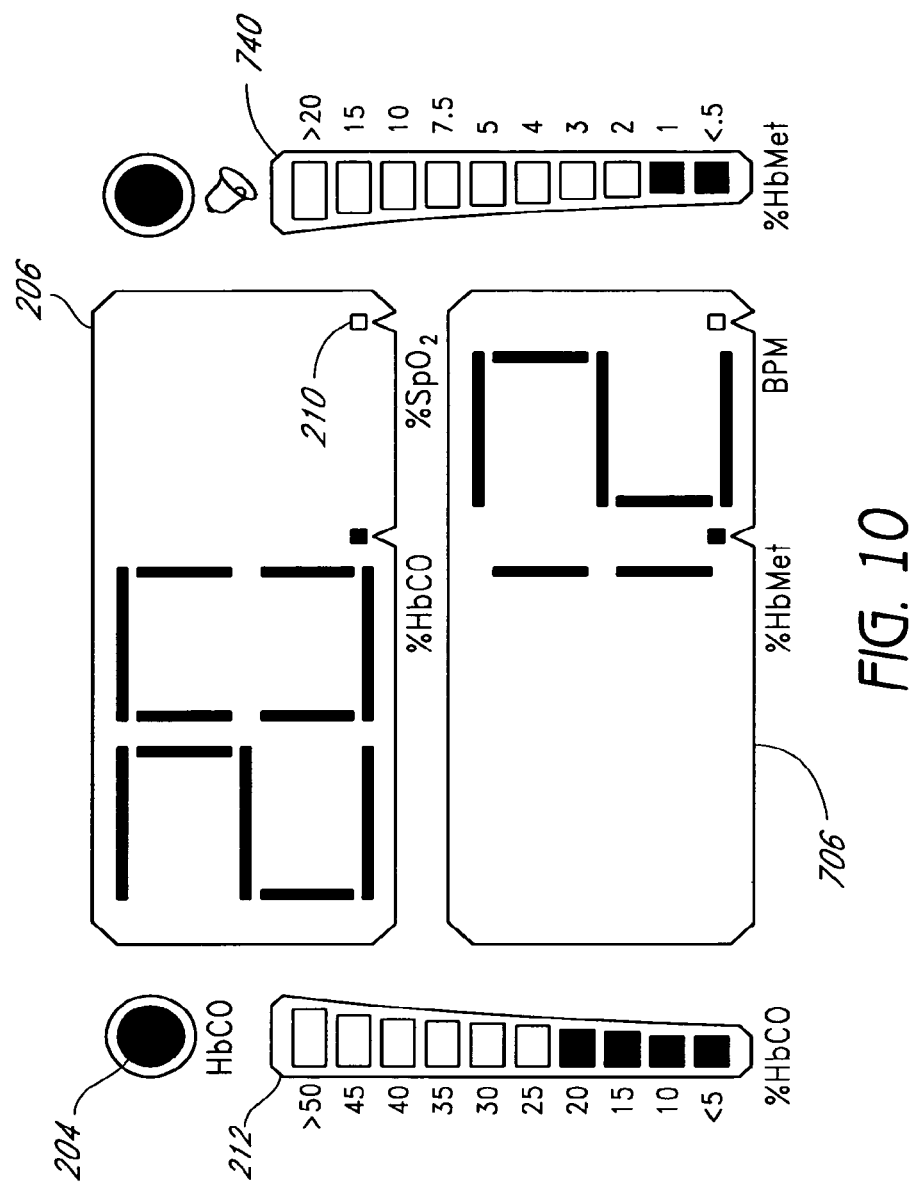
FIG. 10 illustrates the display of FIG. 8 showing measured values of HbCO, HbMet, and type of sensor according to an exemplary embodiment of the patient monitor of FIG. 1.

FIG. 10 illustrates the display of FIG. 8 showing measured values of HbCO, HbMet, and type of sensor according to an exemplary embodiment of the patient monitor of FIG. 1. As shown in FIG. 10, the multi-mode display 706 is displaying a percentage value of HbMet that is shifted using the parameter indicator 708. The data has been advantageously shifted to the left to quickly and efficiently indicate that the displayed parameter is other than BPM. Accordingly, the parameter indicator 708 is also activated to confirm the display of measured values of HbMet. As disclosed in the foregoing, in an embodiment, the multi-mode display 706 is blue.

FIG. 10 also shows the HbMet bar 740 nearly empty, representing acceptable HbMet. In addition, the activation of the HbCO indicator 204 represents communication with a sensor capable of producing sufficient data to determine measured values of HbCO. In an embodiment, such sensors may have appropriate data stored on a memory associated therewith, or the like. FIG. 10 also shows the HbCO measurement being about 20% (as illustrated on the HbCO bar 212 and multi-mode display 206) thereby indicating a potentially dangerous situation that if exacerbated, will become quite problematic. Therefore, the alarm indicator 244 is also activated, and in some embodiments, the speaker 236 as well.

Figure 11A:
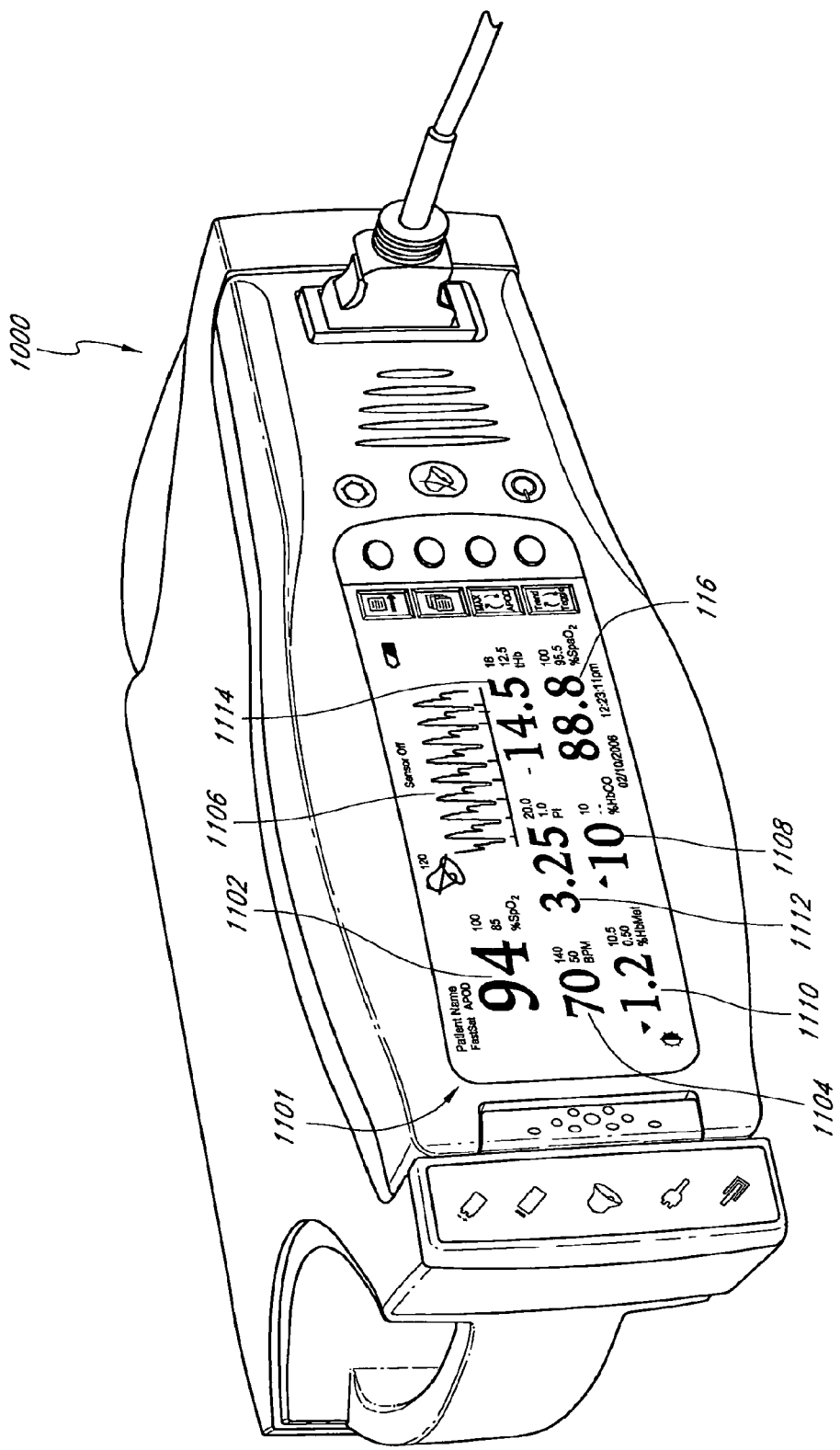
FIG. 11A illustrates a perspective view of an exemplary noninvasive multi-parameter patient monitor such as, for example, the patient monitor of FIG. 1.
Figure 11B:
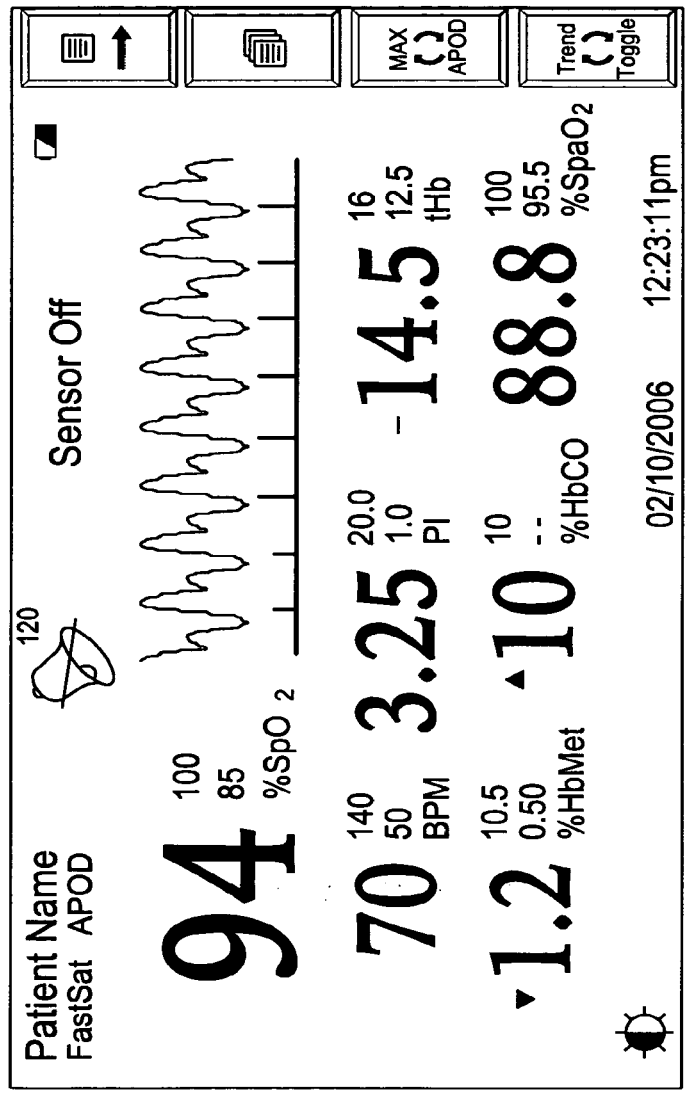
FIGS. 11B-11H illustrate display screens of the patient monitor of FIG. 11A.

FIG. 11A illustrates a perspective view of an exemplary noninvasive multi-parameter patient monitor 1000, such as, for example, the patient monitor of FIG. 1. Moreover, FIGS. 11B-11E illustrate exemplary display screens of the patient monitor of FIG. 11A. As shown in FIGS. 11A-11B, an embodiment of the monitor 1000 includes a display 1101 showing a plurality of parameter data. For example, the display may advantageously comprise a CRT or an LCD display including circuitry similar to that available on oximeters commercially available from Masimo Corporation of Irvine, Calif. sold under the name Radical™, and disclosed in the U.S. patents referenced above and incorporated above. However, an artisan will recognize from the disclosure herein many commercially available display components capable of displaying multiple parameter data along with the ability to display graphical data such as plethysmographs, trend traces, and the like.

In an embodiment, the display includes a measured value of SpO$_2$ 1102, a measured value of pulse rate 1104 in BPM, a plethysmograph 1106, a measured value of HbCO 1108, a measured value of HbMet 1110, a measured value of a perfusion quality 1112, a measured value of Hbt 1114, and a derived value of fractional saturation "SpaO$_2$" 116. In an embodiment, SpaO$_2$ comprises HbO$_2$ expressed as a percentage of the four main hemoglobin species, i.e., HbO$_2$, Hb, HbCO, and HbMet.

In an embodiment, one or more of the foregoing parameter includes trending or prediction indicators 1118 showing the current trend or prediction for that corresponding parameter. In an embodiment, the indicators 1118 may advantageously comprise an up arrow, a down arrow, and a hyphen bar to indicate up trending/prediction, down trending/prediction, or neutral trending/prediction.

Figure 11C:
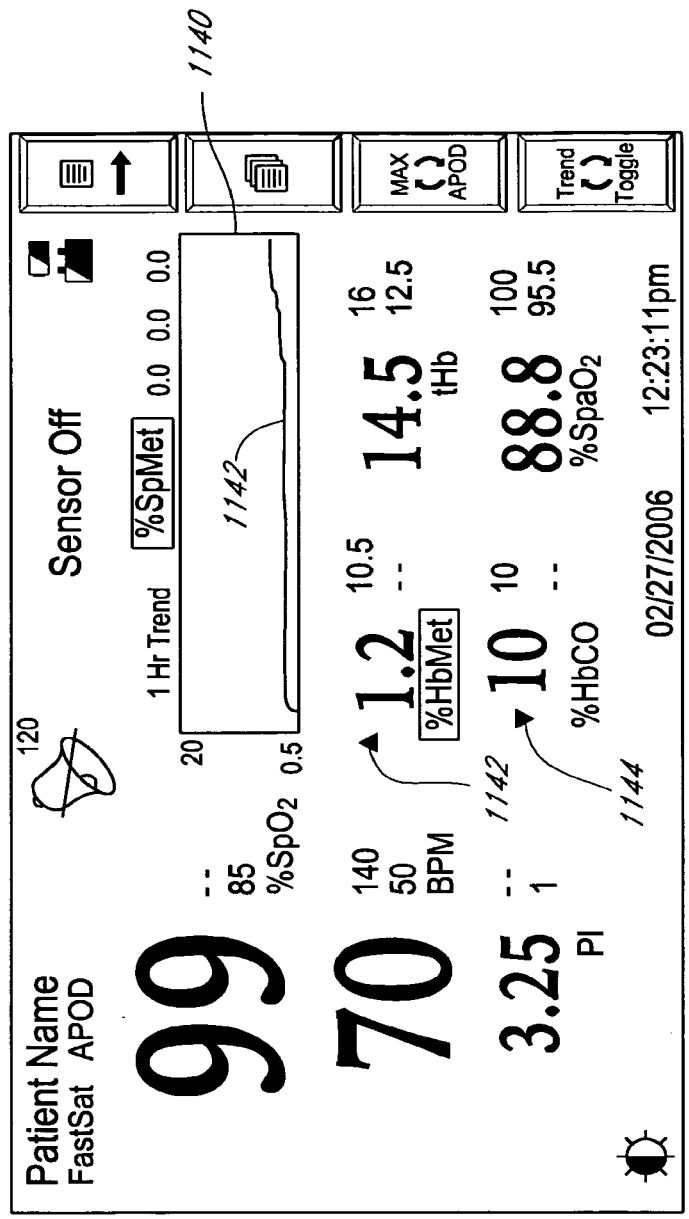

FIG. 11C illustrates an exemplary display screen showing trend graph 1140 including trend line 1142 for HbMet. In an embodiment, the trend line 1142 may be advantageously colored for quick straightforward recognition of the trending parameter, may be associated with any one or more of the foregoing alarm attributes, may include trending lines for other parameters, or the like. The display screen also shows trending directional indicators 1142, 1144 for many of the displayed physiological parameters. In an embodiment, the directional indicators 1142, 1144 may advantageously comprises arrows showing the recent trend, predicted trend, user-customizable trend, combinations thereof, or the like for the associated parameters. In an embodiment, the directional indicators 1142, 1144 comprises an up arrow indicating a rising trend/predicted trend, a middle bar indicating a somewhat stable trend/predicted trend, and a down arrow indicating a lowering trend/predicted trend. An artisan will recognize a wide variety of other directional indicators 1142, 1144 from the disclosure herein.

Figure 11D:
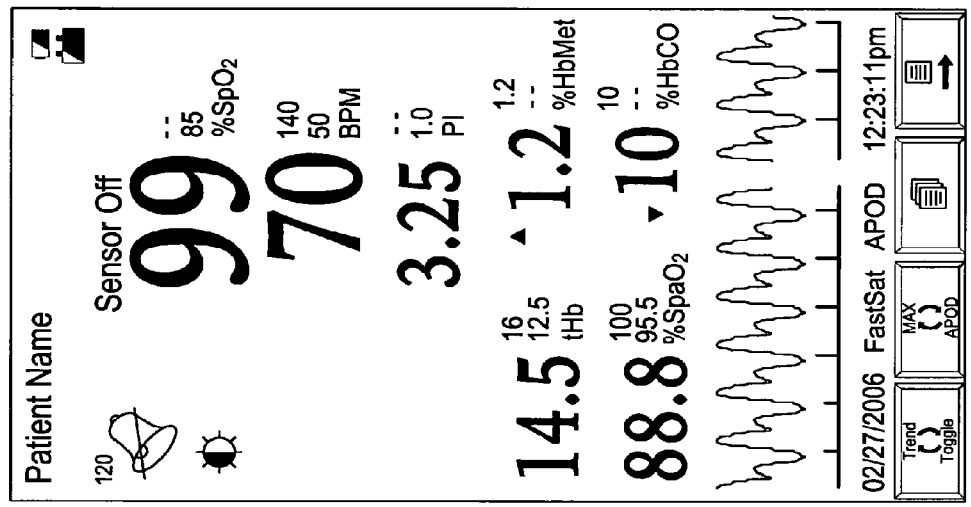
Figure 11E:
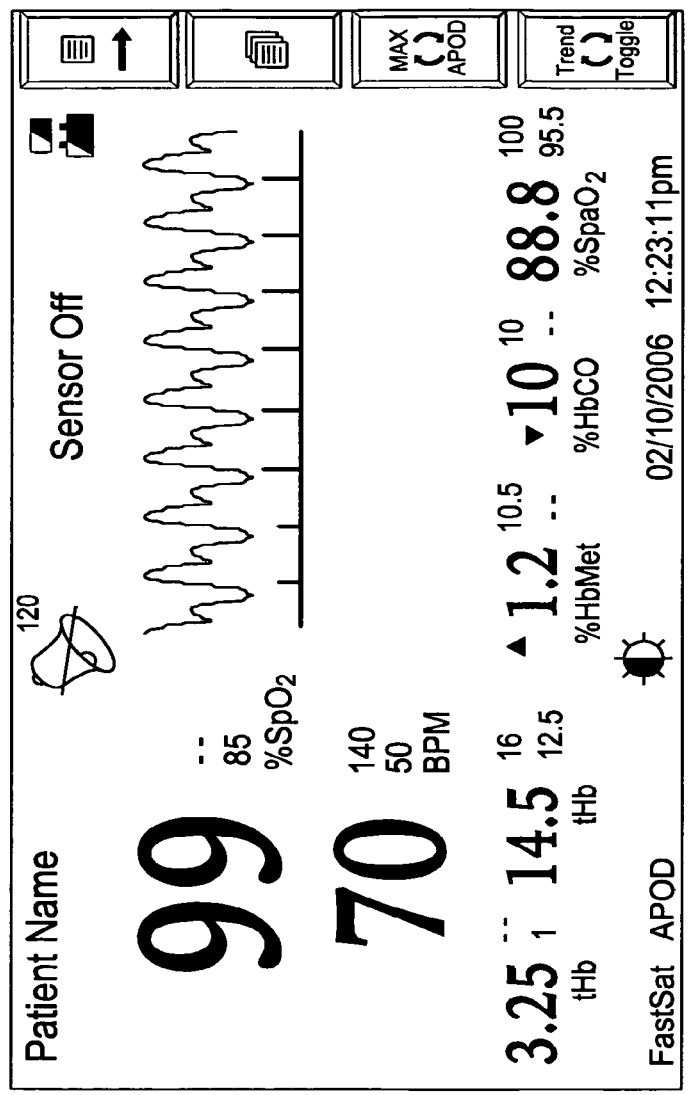
Figure 11F:
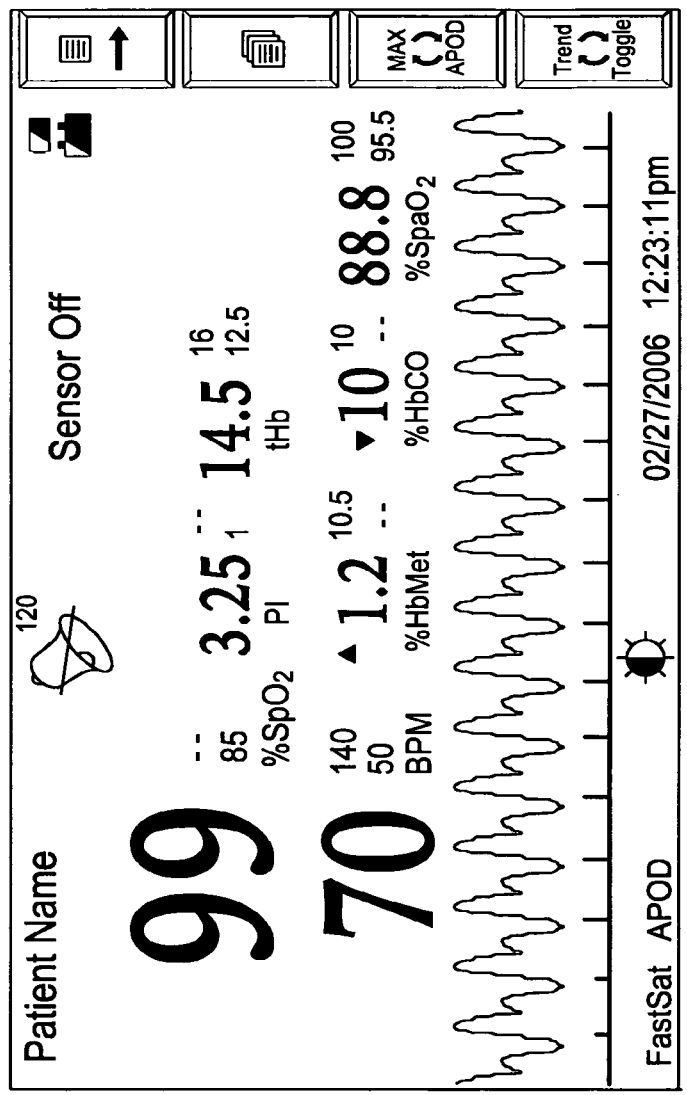
Figure 11G:
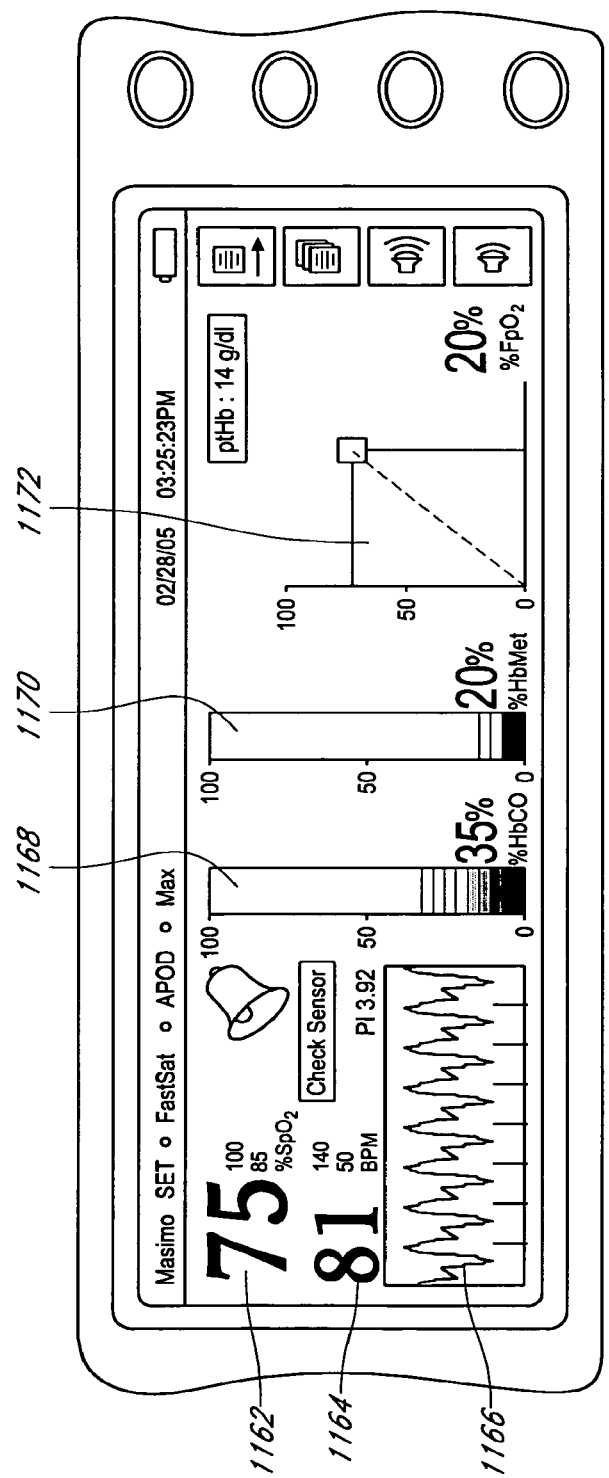
Figure 11H:
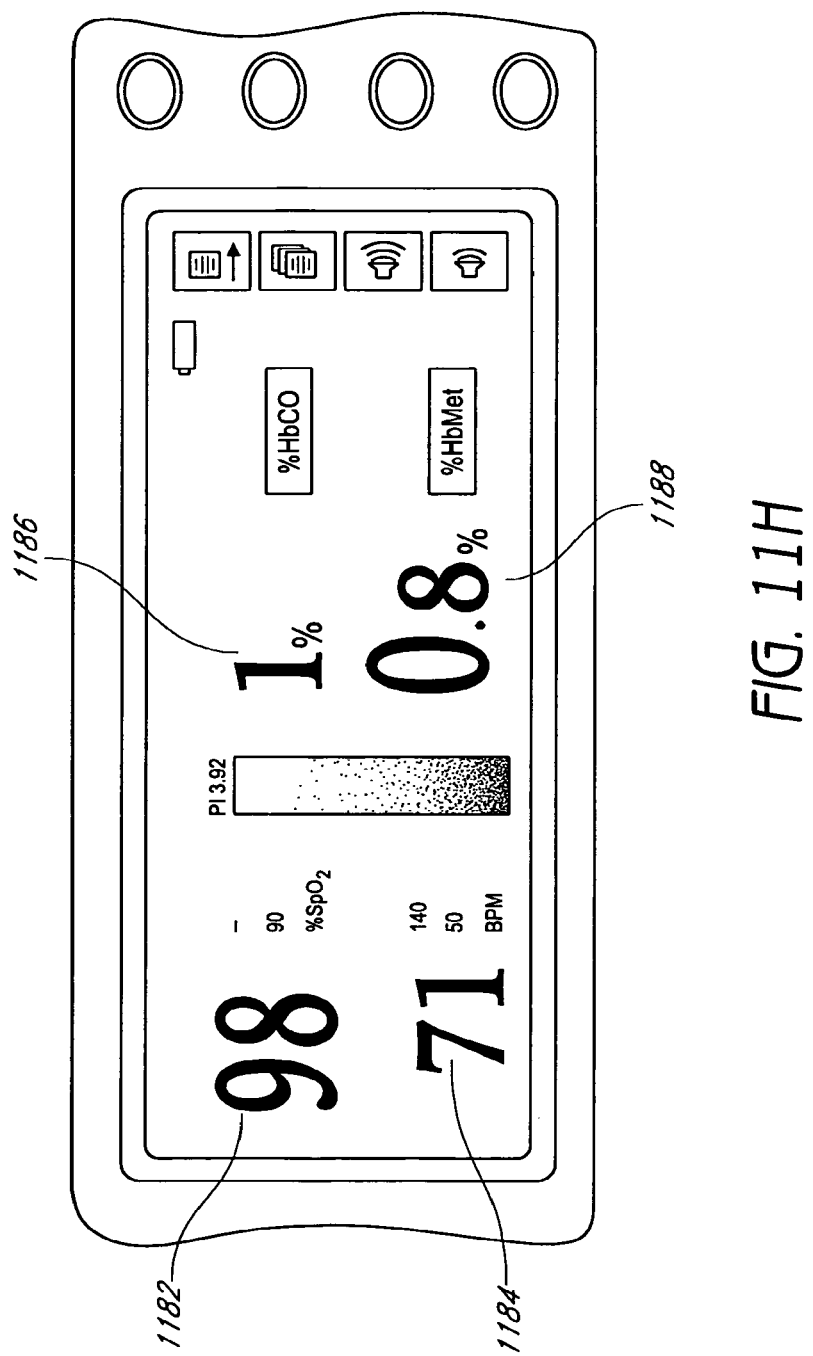

FIG. 11D shows an exemplary display screen in vertical format. Such vertical format could be user actuated or based on a gravity switch. FIGS. 11E-11F illustrate additional displays of various physiological parameters similar to those discussed in the foregoing. being As shown in FIG. 11G, the display includes a measured value of SpO$_2$ 1162, a measured value of pulse rate 1164 in BPM, a plethysmograph 1166, a HbCO bar 1168, and a HbMet bar 1170. In an embodiment, the HbCO bar 1168 and HbMet bar 1170 may advantageously behave the same or similarly to the HbCO bar 212 and HbMet bar 712. Moreover, similar bars may advantageously display any of the physiological parameters discussed herein using display indicia appropriate to that parameter. For example, a $SpO_2$ or $SpaO_2$ bar may advantageously range from about 0% to about 100%, and more preferably range from about 50% to about 100%, while a Hbt bar may advantageously range from about 0 to about 30.

Moreover, similar to the disclosure above, the measured value of $SpO_2$ 1162 may advantageously toggle to measured values of HbCO, HbMet, Hbt, or the like based on, for example, actuation of user input keys, or the like.

In addition to the foregoing, the display may also include graphical data showing one or more color-coded or other identifying indicia for traces of trend data. Moreover, other graphical presentations may advantageously provide readily identifiable indications of monitored parameters or combinations of monitored parameters of the patient. For example, in an embodiment, the display includes a $SpaO_2$ graph 1172. The $SpaO_2$ graph 1172 plots $SpO_2$ as a function of other blood analytes $(1-SpaO_2)$, where $SpaO_2$ comprises $HbO_2$ expressed as a percentage of the four main hemoglobin species, i.e., $HbO_2$, Hb, HbCO, and HbMet. Thus, as shown in FIG. 11C, as the slope of the displayed line or arrow increases, the caregiver can readily note that the majority of hemoglobin carriers are being used to carry oxygen, and not, for example, harmful carbon monoxide. On the other hand, as the slope decreases, the caregiver can readily and advantageously note that the number of hemoglobin species available to carry oxygen is decreasing, regardless of the current value of $SpO_2$. Moreover, the length of the arrow or line also provides an indication of wellness, e.g., the higher the line the more oxygen saturation, the lower the line, the more likely there may be desaturation event, or the like.

Thus, the $SpaO_2$ graph 1172 provides the caregiver with the ability to recognize that even though the measured value of $SpO_2$ may be within acceptable ranges, there are potentially an unacceptable number of hemoglobin carriers unavailable for carrying oxygen, and that other potential problems may exist, such as, for example, harmful carbon monoxide levels, or the like. In an embodiment, various alarm conditions may cause the graph 1172 to change color, flash, or any combination of alarm indications discussed in the forgoing. Moreover, FIG. 11I illustrates yet an additional display of the foregoing parameters.

An embodiment may also include the monitor 1000 advantageously defining regions of wellness/severity of the monitored patient. For example, because the graph 1172 comprises two dimensions, the monitor 1000 may advantageously define regions where the patient's measured physiological parameters are considered acceptable, regions where the patient is considered at risk, regions where the patient is critical, and the like. For example, one region of acceptability may include a high $SpO_2$ and a low $1-SpaO_2$, another region of risk may include a high $SpO_2$ and a high $1-SpaO_2$, and another critical region may include a low $SpO_2$ and a high $1-SpaO_2$. Moreover, an artisan will recognize from the disclosure herein that different parameters may also be combined to provide readily identifiable indications of patient wellness.

In addition to or as an alternative to the two dimensional $SpaO_2$ graph 1172, the monitor 1000 may also include a three dimensional graph, such as, for example, extending the graph 1172 along the variable of time. In this embodiment, the forgoing regions advantageously become three dimensional surfaces of wellness. Moreover, trend data may also be advantageously added to the surface to provide a history of when particular monitored parameters dipped in and out of various surfaces of wellness, risk, criticality, or the like. Such trend data could be color-coded, text identified, or the like. An artisan will also recognize that such surfaces may be dynamic. For example, measurements of HbCO>about 5 may dictate that trend data showing $SpO_2$<about 90% should be considered critical; however, measurements of HbCO<about 5 may dictate only $SpO_2$<about 85% would be critical. Again, an artisan will recognize from the disclosure herein other parameter combinations to create a wide variety of wellness/critical regions or surfaces that provide readily available visual or audio indications of patient well being, trigger specific alarms, or the like.

Moreover, the monitor 1000 may advantageously employ enlargement or reorganization of parameter data based on, for example, the severity of the measurement. For example, the monitor 1000 may display values for HbCO in a small portion of the screen or in the background, and when HbCO begins to approach abnormal levels, the small portion may advantageously grown as severity increases, even in some embodiments to dominate the display. Such visual alarming can be combined with audio alarms such as announcements, alarms, rising frequencies, or the like, and other visual alarms such as flashing, coloration, or the like to assist a caregiver in noticing the increasing severity of a monitored parameter. In an embodiment, a location of the display of an alarming value is changed to be displayed in a larger display area, such as 1102, so as to be readily noticeable and its display values readily ascertainable.

Although the foregoing invention has been described in terms of certain preferred embodiments, other embodiments will be apparent to those of ordinary skill in the art from the disclosure herein. For example, the monitor 100 may advantageously be adapted to monitor or be included in a monitor capable of measuring physiological parameters other than those determined through absorption spectroscopy, such as, for example, blood pressure, ECG, EKG, respiratory rates, volumes, inputs for blood pressure sensors, acoustical sensors, and the like. Moreover, the monitor 100 may be adapted for wireless communication to and from the sensor 106, and/or to and from other monitoring devices, such as, for example, multi-parameter or legacy monitoring devices.

Also, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A method of determining which of a plurality of physiological measurements to measure based on the signal quality of the signal, the method comprising:

using a sensor configured to measure at least two different physiological measurements to obtain a signal from a light sensitive detector, the sensor including at least three different light emitters emitting at least three different wavelengths of light through tissue of a living patient and detecting the light after attenuation of the tissue;

determining a signal quality of the signal;

determining which of the at least two different physiological measurements are capable of being measured based on the signal quality determination; and activating only enough of the at least three different light emitters necessary to obtain the measurements capable of being measured.

2. The method of claim 1, wherein if the signal quality is high, all of the at least three different emitters are activated.

3. The method of claim 1, wherein if the signal quality is low, only two of the at least three different emitters are activated.

4. The method of claim 1, wherein if the signal quality is low, fewer different physiological measurements are measured.

5. A method of informing a user of a patient monitor about one of a type of sensor communicating with the patient monitor and a type of physiological parameter determinable using the sensor communicating with the patient monitor, the method comprising:

receiving information from an information element associated with one of an optical sensor and a communication cable between a patient monitor and an optical sensor;

determining a number of wavelengths emitted by the optical sensor from the information;

determining a signal quality of a signal received by the optical sensor; and activating an indicator of the type of physiological parameters determinable based on the number wavelengths emitted by the optical sensor and the signal quality of the signal.

6. The method of claim 5, wherein the indicator comprises a display of data determined using signals from the optical sensor.

7. The method of claim 5, wherein the indicator comprises a visual indicator.

8. The method of claim 7, wherein the visual indicator comprises a color.

9. The method of claim 7, wherein the visual indicator comprises an LED.

10. The method of claim 9, wherein the LED changes color based on which of the first and second sensors is attached.

11. The method of claim 9, wherein the LED color comprises red when the first sensor is attached and another color when another sensor is attached.

12. The method of claim 5, wherein the indicator comprises an audible indicator.

13. The method of claim 12, wherein the audible indictor comprises one or more tones.

14. The method of claim 12, wherein the audible indictor emits a first tone when the first sensor is attached and a different second tone when the second sensor is attached.

15. A physiological parameter monitor capable of improving performance by activating more light emission sources of an optical sensor, the monitor comprising a processor capable of determining a number of light emission sources available for activation on an attached sensor and capable of activating two of the plurality of light emission sources and capable of activating more than two of the plurality of light emission sources based on a signal quality received from the optical sensor.

16. The monitor of claim 15, wherein the processor activates two of the plurality of light emission sources to measure a first physiological parameter under low signal quality conditions.

17. The monitor of claim 16, wherein the processor activates more than two of the plurality of light emission sources to measure a second physiological parameter under high signal quality conditions.

18. The monitor of claim 16, wherein the processor activates more than two of the plurality of light emission sources to more accurately measure the first physiological parameter.

19. The monitor of claim 15, wherein the processor activates more than two of the plurality of light emission sources to measure a second physiological parameter.

* * * * *